US009845471B2

(12) United States Patent
Hingorani

(10) Patent No.: US 9,845,471 B2
(45) Date of Patent: Dec. 19, 2017

(54) COMPOSITIONS AND METHODS FOR TREATING PANCREATIC CANCER

(71) Applicant: Fred Hutchinson Cancer Research Center, Seattle, WA (US)

(72) Inventor: Sunil R. Hingorani, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

(21) Appl. No.: 14/760,940

(22) PCT Filed: Jan. 14, 2014

(86) PCT No.: PCT/US2014/011536
§ 371 (c)(1),
(2) Date: Jul. 14, 2015

(87) PCT Pub. No.: WO2014/113406
PCT Pub. Date: Jul. 24, 2014

(65) Prior Publication Data
US 2015/0368646 A1    Dec. 24, 2015

Related U.S. Application Data

(60) Provisional application No. 61/752,819, filed on Jan. 15, 2013.

(51) Int. Cl.
| C12N 15/11 | (2006.01) |
| C12N 15/113 | (2010.01) |
| A61K 31/713 | (2006.01) |
| A61K 45/06 | (2006.01) |
| A61K 38/00 | (2006.01) |

(52) U.S. Cl.
CPC ........ *C12N 15/1135* (2013.01); *A61K 31/713* (2013.01); *A61K 45/06* (2013.01); *C12N 15/113* (2013.01); *A61K 38/00* (2013.01); *C12N 2310/11* (2013.01); *C12N 2310/14* (2013.01); *C12N 2320/30* (2013.01); *C12N 2320/31* (2013.01); *C12N 2740/15041* (2013.01)

(58) Field of Classification Search
None
See application file for complete search history.

(56) References Cited

U.S. PATENT DOCUMENTS

| 2004/0146986 A1 | 7/2004 | Bae et al. | |
| 2010/0227319 A1* | 9/2010 | Hoon ................... | C12Q 1/6886 435/6.14 |
| 2012/0309706 A1* | 12/2012 | Moussy ............... | A61K 31/136 514/49 |

FOREIGN PATENT DOCUMENTS

WO    2006/057623    6/2006

OTHER PUBLICATIONS

Gansauge et al., Overexpression of cyclin D1 in human pancreatic carcinoma is associated with poor prognosis, 1997, Cancer Research, vol. 57, pp. 1634-1637.*
Schwarte-Waldhoff et al., Smad4/DPC4-mediated tumor suppression through suppression of angiogenesis, 2000, PNAS, vol. 97, pp. 9624-9629.*
Whittle et al., RUNX3 controls a metastatic switch in pancreatic ductal adenocarcinoma, 2015, Cell, vol. 161, pp. 1345-1360.*
Armstrong et al., "Type I Collagen Promotes the Malignant Phenotype of Pancreatic Ductal Adenocarcinoma," *Clinical Cancer Research 10*:7427-7437, 2004.
Bae et al., "Phosphorylation, acetylation and ubiquitination: The molecular basis of RUNX regulation," *Gene 366*:58-66, 2006.
Bae et al., "Tumor suppressor activity of RUNX3," *Oncogene 23*:4336-4340, 2004.
Blyth et al., "The RUNX Genes: Gain or Loss of Function in Cancer," *Nature Reviews Cancer 5*:376-387, 2005.
Bonaldo et al., "Structural and Functional Features of the α3 Chain Indicate a Bridging Role for Chicken Collagen VI in Connective Tissues," *Biochemistry 29*:1245-1254, 1990.
Bradshaw, "The role of SPARC in extracellular matrix assembly," *Journal of Cell Commun. Signal.3*:239-246, 2009.
Chi et al., "Runt-Related Transcription Factor RUNX3 Is a Target of MDM2-Mediated Ubiquitination," *Cancer Research 69*(20): 8111-8119, 2009.
Debernardi et al., "Genome-wide Analysis of Acute Myeloid Leukemia With Normal Karyotype Reveals a Unique Pattern of Homeobox Gene Expression Distinct From Those With Translocation-Mediated Fusion Events," *Genes, Chromosomes & Cancer 37*:149-158, 2003.
Ding et al., "SMAD4-dependent barrier constrains prostate cancer growth and metastatic progression," *Nature 470*:269-273, 2011.
Dudley et al., "Calcification of Multipotent Prostate Tumor Endothelium," *Cancer Cell 14*:201- 211, 2008.
Hruban et al., "Progression Model for Pancreatic Cancer," *Clinical Cancer Research 6*:2969-2972, 2000.
Ito et al., "RUNX Genes in Development and Cancer: Regulation of Viral Gene Expression and the Discovery of RUNX Family Genes," *Advances in Cancer Research 99*:33-76, 2008.
Ito et al., "Runx3 expression in gastrointestinal tract epithelium: resolving the controversy," *Oncogene 28*:1379-1384, 2009.
Jin et al., "Transforming Growth Factor-β Stimulates p300-dependent RUNX3 Acetylation, Which Inhibits Ubiquitination-mediated Degradation," *Journal of Biological Chemistry 279*(28):29409-29417, 2004.
Kielty et al., "Type VI Collagen Microfibrils: Evidence for a Structural Association with Hyaluronan," *Journal of Cell Biology 118*(4):979-990, 1992.
Kim et al., "Carcinoma-produced factors activate myeloid cells through TLR2 to stimulate metastasis," *Nature 457*:102-106, 2009.
Kolb et al., "Osteopontin influences the invasiveness of pancreatic cancer cells and is increased in neoplastic and inflammatory conditions," *Cancer Biology & Therapy 4*(7):740-746, 2005.

(Continued)

*Primary Examiner* — Dana Shin
(74) *Attorney, Agent, or Firm* — Seed IP Law Group LLP

(57) ABSTRACT

The present disclosure provides compositions and methods for treating or reducing the risk of pancreatic cancer by administering compounds capable of inhibiting the expression or activity of RUNX3.

5 Claims, 14 Drawing Sheets

(56) References Cited

OTHER PUBLICATIONS

Krantz et al., "MT1-MMP Cooperates with Kras$^{G12D}$ to Promote Pancreatic Fibrosis through Increased TDF-β Signaling," *Molecular Cancer Research* 9(10):1294-1304, 2011.

Lacayo et al., "Gene expression profiles at diagnosis in de novo childhood AML patients identify FLT3 mutations with good clinical outcomes," *Blood* 104(9):2646-2654, 2004.

Lee et al., "Expression of RUNX3 in skin cancers," *Clinical and Experimental Dermatology* 36:769-774, 2011.

Lee et al., "RUNX3 functions as an oncogene in ovarian cancer," *Gynecologic Oncology* 122:410-417, 2011.

Levanon et al., "Absence of Runx3 expression in normal gastrointestinal epithelium calls into question its tumour suppressor function," *EMBO Molecular Medicine* 3:593-604, 2011.

Levanon et al., "Spatial and temporal expression pattern of Runx3 (Am12) and Runx1 (Aml 1) indicates non-redundant functions during mouse embryogenesis," *Mechanisms of Development* 109:413-417, 2001.

Li et al., "Causal Relationship between the Loss of RUNX3 Expression and Gastric Cancer," *Cell* 109:113-124, 2002.

Li et al., "RUNX3 expression in primary and metastatic pancreatic cancer," *Journal of Clinical Pathology* 57:294-299, 2004.

McDevitt et al., "Interaction of intact type VI collagen with hyaluronan," *Federation of European Biochemical Societies Letters* 294(3):167-170, 1991.

Osaki et al., "Expression of RUNX3 protein in human gastric mucosa, intestinal metaplasia and carcinoma," *European Journal of Clinical Investigation* 34:605-612, 2004.

Pan et al., "Proteomics Portrait of Archival Lesions of Chronic Pancreatitis,"*PLoS One* 6(11):e27574, 2011. (12 pages).

Poultsides et al., "Histopathologic Basis for the Favorable Survival after Resection of Intraductal Papillary Mucinous Neoplasm-Associated Invasive Adenocarcinoma of the Pancreas," *Annals of Surgery* 251(3):470-476, 2010.

Said et al., "RhoGDI2 suppresses lung metastasis in mice by reducing tumor versican expression and macrophage infiltration," *Journal of Clinical Investigation* 122(4):1503-1518, 2012.

Salto-Tellez et al., "RUNX3 protein is overexpressed in human basal cell carcinomas," *Oncogene* 25:7646-7649, 2006.

Schelter et al., "Tumor cell-derived Timp-1 is necessary for maintaining metastasis-promoting Met-signaling via inhibition of Adam-10," *Clinical & Experimental Metastasis* 28:793-802, 2011.

Shields et al., "Biochemical role of the collagen-rich tumour microenvironment in pancreatic cancer progression," *Biochemistry Journal* 441:541-552, 2012.I Shintain et al., "Collagen I Promotes Metastasis in Pancreatic Cancer by Activating c-Jun NH$_2$-Terminal Kinase 1 and Up-regulating N-Cadherin Expression," *Cancer Research* 66(24):11745-11753, 2006.

Speck et al., "Core-Binding Factor: A Central Player in Hematopoiesis and Leukemia," *Cancer Research (Supplement)* 59:1789s-1793s, 1999.

Tsunematsu et al., RUNX3 Has an Oncogenic Role in Head and Neck Cancer, *PLoS One* 4(6):e5829, 2009. (12 pages).

Yarmus et al., "Groucho/transducing-like Enhancer-of-split (TLE)-dependent and -independent transcriptional regulation by Runx3," *Proceedings of the National Academy of Sciences* 103(19):7384-7389, 2006.

Yu et al., "Stable Isotope Dilution Multidimensional Liquid Chromatography-Tandem Mass Spectrometry for Pancreatic Cancer Serum Biomarker Discovery," *Journal of Proteome Research* 8:1565-1576, 2009.

\* cited by examiner

SEQUENCE LISTING

<160> NUMBER OF SEQ ID NOS: 20

<210> SEQ ID NO 1
<211> LENGTH: 19
<212> TYPE: DNA
<213> ORGANISM: Artificial Sequence
<220> FEATURE:
<223> OTHER INFORMATION: Short hairpin target sequence

<400> SEQUENCE: 1
gattaacact gcagagtaa                                              19

<210> SEQ ID NO 2
<211> LENGTH: 35
<212> TYPE: DNA
<213> ORGANISM: Artificial Sequence
<220> FEATURE:
<223> OTHER INFORMATION: oligonucleotide sequence designed to span two
      putative consensus Runx3 binding sites

<400> SEQUENCE: 2
ggtccctcaa ccacagaacc acaaggccag gccct                            35

<210> SEQ ID NO 3
<211> LENGTH: 35
<212> TYPE: DNA
<213> ORGANISM: Artificial Sequence
<220> FEATURE:
<223> OTHER INFORMATION: oligonucleotide sequence designed to span two
      putative consensus Runx3 binding sites

<400> SEQUENCE: 3
ccagggagtt ggtgtcttgg tgttccggtc cggga                            35

<210> SEQ ID NO 4
<211> LENGTH: 19
<212> TYPE: DNA
<213> ORGANISM: Artificial Sequence
<220> FEATURE:
<223> OTHER INFORMATION: Short hairpin target sequence

<400> SEQUENCE: 4
cggcagaagc tggaggacc                                              19

<210> SEQ ID NO 5
<211> LENGTH: 22
<212> TYPE: DNA
<213> ORGANISM: Artificial Sequence
<220> FEATURE:
<223> OTHER INFORMATION: Primer sequence

<400> SEQUENCE: 5
tttcactcca atcgtcccta ca                                          22

<210> SEQ ID NO 6
<211> LENGTH: 23
<212> TYPE: DNA
<213> ORGANISM: Artificial Sequence
<220> FEATURE:
<223> OTHER INFORMATION: Primer sequence

<400> SEQUENCE: 6
tcagtccata agccaagcta tca                                         23

<210> SEQ ID NO 7
<211> LENGTH: 19
<212> TYPE: DNA
<213> ORGANISM: Artificial Sequence
<220> FEATURE:
<223> OTHER INFORMATION: Primer sequence

<400> SEQUENCE: 7
ctgctgctac aagcctgct                                                    19

<210> SEQ ID NO 8
<211> LENGTH: 19
<212> TYPE: DNA
<213> ORGANISM: Artificial Sequence
<220> FEATURE:
<223> OTHER INFORMATION: Primer sequence

<400> SEQUENCE: 8
ctgctgctac aagcctgct                                                    19

<210> SEQ ID NO 9
<211> LENGTH: 20
<212> TYPE: DNA
<213> ORGANISM: Artificial Sequence
<220> FEATURE:
<223> OTHER INFORMATION: Primer sequence

<400> SEQUENCE: 9
acaccgactg cgctatcaag                                                   20

<210> SEQ ID NO 10
<211> LENGTH: 22
<212> TYPE: DNA
<213> ORGANISM: Artificial Sequence
<220> FEATURE:
<223> OTHER INFORMATION: Primer sequence

<400> SEQUENCE: 10
cggtcaccac aatcaggtac tt                                                22

<210> SEQ ID NO 11
<211> LENGTH: 22
<212> TYPE: DNA
<213> ORGANISM: Artificial Sequence
<220> FEATURE:
<223> OTHER INFORMATION: Primer sequence

<400> SEQUENCE: 11
gagctgtttg cagacaaagt tc                                                22

<210> SEQ ID NO 12
<211> LENGTH: 20
<212> TYPE: DNA
<213> ORGANISM: Artificial Sequence
<220> FEATURE:
<223> OTHER INFORMATION: Primer sequence

<400> SEQUENCE: 12
ccctggcaca tgaatcctgg                                                   20

<210> SEQ ID NO 13
<211> LENGTH: 21
<212> TYPE: DNA
<213> ORGANISM: Artificial Sequence
<220> FEATURE:
<223> OTHER INFORMATION: Primer sequence

<400> SEQUENCE: 13
cccaccgtgt tcttcgacat t              21

<210> SEQ ID NO 14
<211> LENGTH: 22
<212> TYPE: DNA
<213> ORGANISM: Artificial Sequence
<220> FEATURE:
<223> OTHER INFORMATION: Primer sequence

<400> SEQUENCE: 14
ggacccgtat gctttaggat ga             22

<210> SEQ ID NO 15
<211> LENGTH: 18
<212> TYPE: DNA
<213> ORGANISM: Artificial Sequence
<220> FEATURE:
<223> OTHER INFORMATION: Primer sequence

<400> SEQUENCE: 15
agcccaccac gttctttg                  18

<210> SEQ ID NO 16
<211> LENGTH: 21
<212> TYPE: DNA
<213> ORGANISM: Artificial Sequence
<220> FEATURE:
<223> OTHER INFORMATION: Primer sequence

<400> SEQUENCE: 16
gtcatcacgg ctgtcatagg g              21

<210> SEQ ID NO 17
<211> LENGTH: 20
<212> TYPE: DNA
<213> ORGANISM: Artificial Sequence
<220> FEATURE:
<223> OTHER INFORMATION: Primer sequence

<400> SEQUENCE: 17
agagtttcac gctcacaatc                20

<210> SEQ ID NO 18
<211> LENGTH: 18
<212> TYPE: DNA
<213> ORGANISM: Artificial Sequence
<220> FEATURE:
<223> OTHER INFORMATION: Primer sequence

<400> SEQUENCE: 18
ggagaagggg ttcaggtc                  18

<210> SEQ ID NO 19
<211> LENGTH: 19
<212> TYPE: RNA
<213> ORGANISM: Artificial Sequence
<220> FEATURE:
<223> OTHER INFORMATION: Short hairpin target sequence

<400> SEQUENCE: 19
gauuaacacu gcagaguaa                 19

<210> SEQ ID NO 20

```
<211> LENGTH: 19
<212> TYPE: RNA
<213> ORGANISM: Artificial Sequence
<220> FEATURE:
<223> OTHER INFORMATION: Short hairpin target sequence

<400> SEQUENCE: 20
cggcagaagc uggaggacc                                                   19
```

COMPOSITIONS AND METHODS FOR TREATING PANCREATIC CANCER

CROSS REFERENCE TO RELATED APPLICATION

This application claims the benefit under 35 U.S.C. §119(e) to U.S. Provisional Application 61/752,819 filed Jan. 15, 2013, which application is incorporated by reference herein in its entirety.

STATEMENT OF GOVERNMENT INTEREST

This invention was made with government support under Grant Nos. CA129357 and CA114028, awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_413USPC_SEQUENCE_LISTING.txt. The text file is 4.2 KB, was created on Jul. 14, 2015, and is being submitted electronically via EFS-Web.

BACKGROUND

Technical Field

The present disclosure provides compositions and methods for treating or reducing the risk of pancreatic cancer and, more specifically, compounds capable of inhibiting the expression or activity of RUNX3 that are useful in minimizing or eliminating the metastasis of pancreatic cancer.

Description of the Related Art

Patients with carcinomas die of metastatic disease. Rarely do they succumb because of the primary tumor alone. This is especially true of pancreatic ductal adenocarcinoma or, more commonly, pancreas cancer. Pancreas cancers appear to calibrate the often competing needs of local growth and distant spread to generate a profoundly lethal disease. While early metastasis characterizes the majority of clinical presentations, extension of locally invasive disease in others not only precludes surgical resection, but can also lead to demise.

Pancreatic ductal adenocarcinomas (PDAs) are thought to initiate most commonly in precursor lesions, termed pancreatic intraepithelial neoplasias (PanINs), which arise in the terminal ductules (Hruban et al., *Am. J. Surg. Pathol.* 25:579, 2001). Activating mutations in the KRAS proto-oncogene occur early in preinvasive disease and are almost uniformly present (>90%) in invasive PDA. Mutations in CDKN2A/INK4A are similarly abundant in invasive disease (>95%) and point mutations in TP53 are also extremely common (>75%). Mutations in DPC4/SMAD4, the last of the cardinal genetic events associated with PDA, occur late in the PanIN-to-PDA progression scheme and are ultimately found in approximately 50% of invasive cancers (Hruban et al., *Clin. Cancer Res.* 6:2969, 2000).

Ductal adenocarcinomas of the pancreas can also arise from two clinically, histologically, and genetically distinct classes of macroscopic cystic precursors, intraductal papillary mucinous neoplasms (IPMN) and mucinous cystic neoplasms (MCN) (Hruban et al., *Gastroenterology Clinics of North America* 36:831, 2007). Interestingly, although both MCNs and IPMNs can culminate in invasive PDA, the carcinomas that arise from these cystic routes portend significantly better prognoses for patients than the classical route (Hingorani, *Gastroenterology* 133:345, 2007; Hruban, 2007; Poultsides et al., *Ann. Surg.* 251:470, 2010).

Pancreatic cancer is an unusually lethal disease with the highest 1-year and 5-year mortality rates of any cancer. Notoriously difficult to detect and resistant to all current therapeutic modalities, PDA has already advanced locally or frankly metastasized in most patients at the time of diagnosis; median survival in this setting is approximately 6 months (Hidalgo, *New England J. Med.* 362:1605, 2010). For the fortunate few for whom surgical resection is possible, median survival increases to 2 years but is not durable: survival at 5 years is only 20% and continues to decline to less than 2% at 10 years (Allison et al., *J. Surg. Oncol.* 67:151, 1998). The majority of these resected patients also eventually die of metastatic disease, which indicates that clinical Stage I tumors are, in fact, already micrometastatic Stage IV. In this regard, PDA is unlike any other major epithelial malignancy, or solid tumor for that matter, in which chronologically distinct stages of disease permit meaningful surgical interventions that can prolong survival and even effect cures.

Hence, there remains a need in the art for alternative therapies and methods for reducing the risk of or treating pancreatic cancer and associated disorders. The present disclosure meets such needs, and further provides other related advantages.

BRIEF SUMMARY

In one aspect, the present disclosure provides methods for reducing the risk of or treating pancreatic cancer, metastasized pancreatic cancer, pancreatic cancer precursor lesions, or a metastatic niche associated with pancreatic cancer with a RUNX3 inhibitor, an agent capable of blocking the association of RUNX3 with a second transcription factor, an agent that enhances deacetylation of RUNX3, an agent that enhances ubiquitination of RUNX3, or any combination thereof.

These methods may be used as adjuvant or neoadjuvant therapies with existing therapies, such as surgery (e.g., Whipple operation), chemotherapy, radiation therapy, chemoradiation therapy, or any combination thereof. The RUNX3 inhibitors may also be used in combination with other active agents, such as expression or activity inhibitors of Bmpr1a, Smad5, Tgfb3, Smad4, Bmp1, Itgb7, Tgfb1i1, Bmper, Ltbp1, Ltbp2, Itgb5, Id1, Tgfbi, Dlx2, Ctgf, Selp, Timp2, Col5a1, Ncam1, Thbs3, Mmp11, Sgce, Fn1, Vcam1, Ecm1, Adamts1, Mmp2, Thbs1, FblnI, Tgfbi, Cdh2, Mmp10, Timp3, Spp1, Vcan, Sparc, Col6a1, cyclin D, cyclin E, or any combination thereof, or in combination with conventional chemotherapies such as gemcitabine, nanoparticle albumin bound (nab)-paclitaxel, FOLFIRINOX combination (5-fluorouracil, leucovorin, irinotecan and oxaliplatin) or any combination thereof.

Trp53$^{LSL-R172H/+}$::Dpc4$^{flox/+}$::p48$^{Cre/+}$ (KPD) mice. (B) Kaplan-Meier survival curves of KP, KPD, and control cohorts. Survival of KPD animals (151 days) is significantly less than control animals (p<0.001) and Kras$^{LSL-G12D/+}$::DpC4$^{flox/+}$::p48$^{Cre/+}$ (KD) mice (p<0.001), but not significantly different from KP mice (147 days, p=0.28). A log rank test was used for each pair wise combination.

Figure 2:
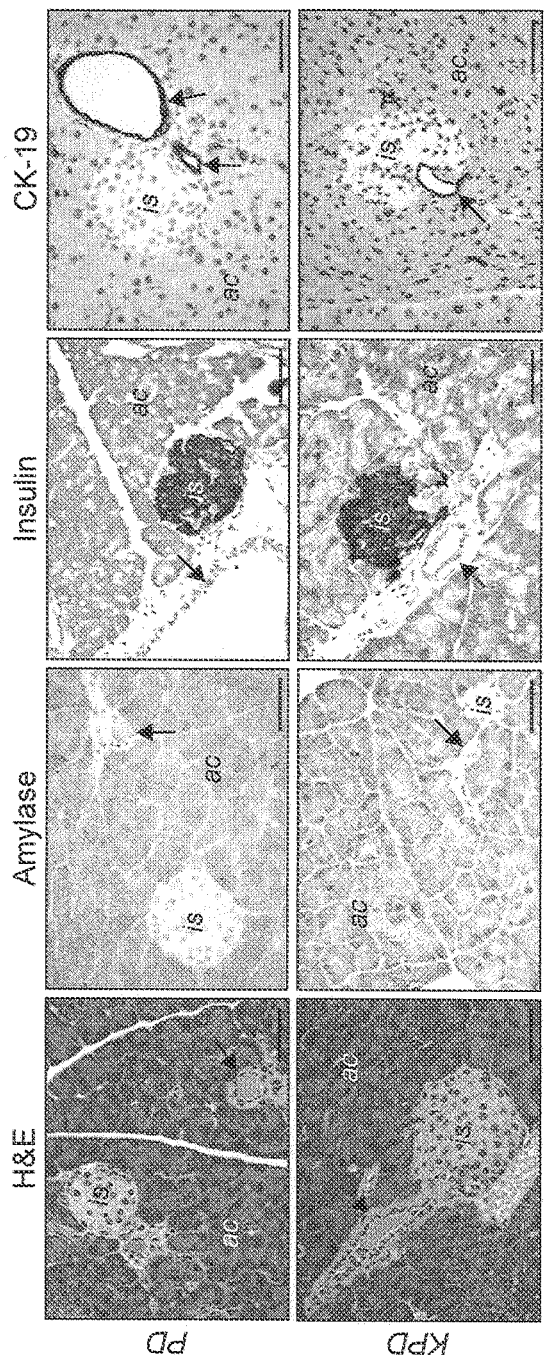

FIG. 2 shows the architectural and functional integrity of pancreata in PD and KPD animals. Immunohistochemical detection of digestive enzymes (amylase), hormones (insulin) and surface markers (CK-19) in distinct compartments of the pancreas from Trp53$^{LSL-R172H/+}$::Dpc4$^{flox/+}$::p48$^{Cre/+}$ (PD) and Kras$^{LSL-G12D/+}$::Trp53$^{LSL-R172H/+}$::Dpc4$^{flox/+}$::p48$^{Cre/+}$ (KPD) and animals. (is, islets; ac, acini; arrow, ducts. Scale bars, 50 µm.)

Figure 3:
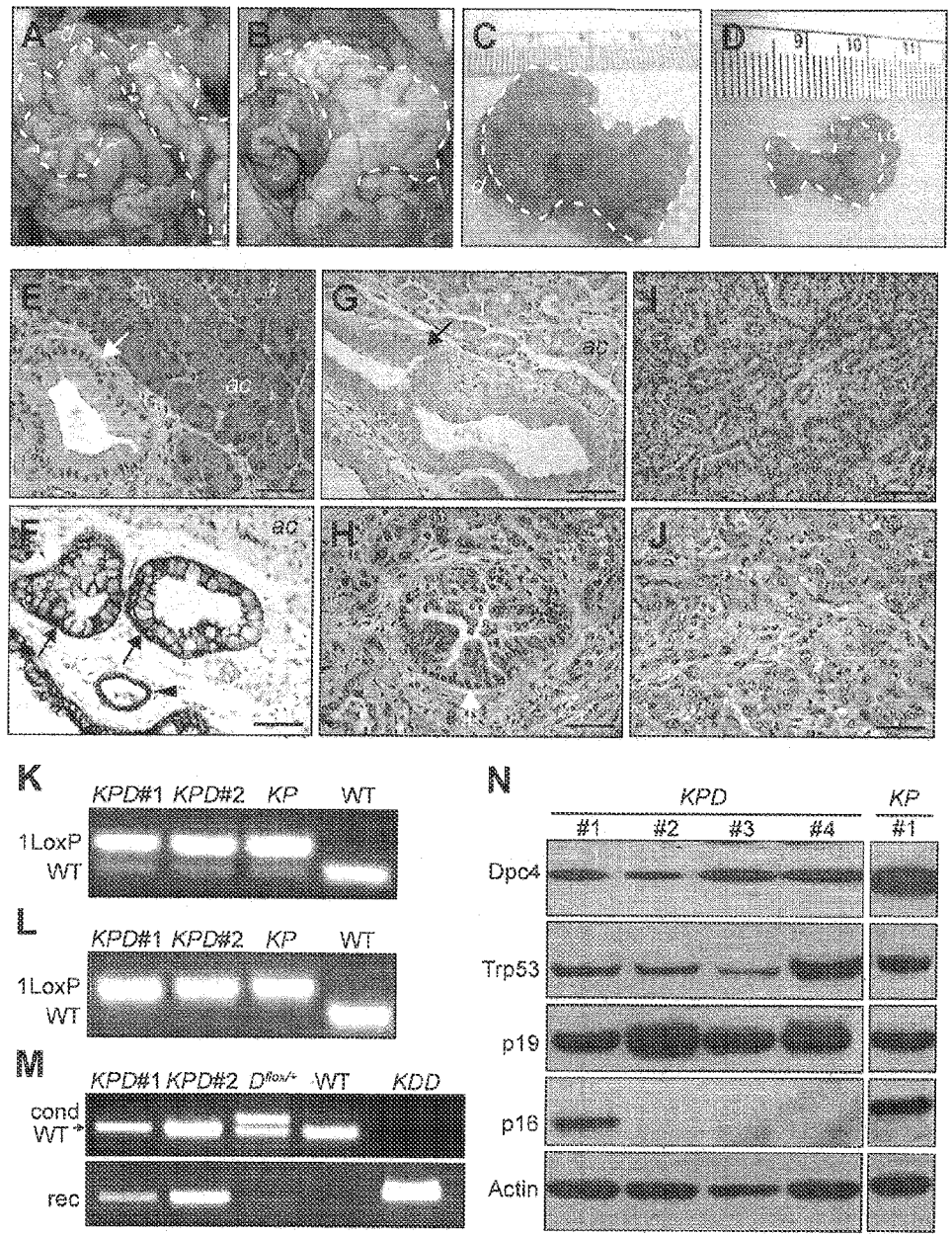

FIGS. 3A-3N show the histological and molecular characterization of tumor progression in KPD mice. (A and B) Gross pathology of moribund KPD mice at necropsy. Dashed lines outline tumor. (C) Representative resected KPD tumor. (D) Representative resected KP tumor. (E) Histology of pancreas in a young KPD animal. Arrow indicates PanIN-1A lesion. (F) CK-19 staining in KPD animal. Arrows, PanIN-2; arrowhead, PanIN-1. (G) Alcian blue staining (arrow) in a well-differentiated area of PDA from KPD animal. (H) Histology of pancreas in an older KPD animal. Arrow indicates PanIN-3 lesion. (I) Moderately well-differentiated histology in a KPD PDA. (J) Poorly differentiated PDA from a KPD animal. (K) Evidence of recombined Kras$^{L-G12D}$ allele (1LoxP, upper band) and wild type (lower band) alleles in primary cells from KPD and KP tumors. (L) Evidence of recombined Trp53$^{L-R172H}$ allele (1LoxP, upper band) and uniform loss of wild type Trp53 (lower band) in primary carcinoma cells from KPD and KP animals. (M) Conditional (cond) Dpc4 allele was recombined (rec) and the wild type (WT) allele retained in all KPD primary cells lines. WT, D$^{flox/+}$ and KDD represent controls for various alleles. (N) Immunoblots of lysates from purified KPD and KP primary PDA cells for the indicated proteins. d, duodenum; ac, acinar cells. Scale bars, 50 µm. See also Table S1.

FIGS. 4A-4G show how heterozygous loss of Dpc4 affects proliferation and cell cycle control. (A) Ki-67 expression in KPD PDA. (B) Ki-67 expression in KP PDA. (C) Cleaved caspase 3 (CC3) detection in KPD PDA. (D) Cleaved caspase 3 (CC3) detection in KP PDA. (E) Quantification of Ki-67 expression in KPD and KP tumor sections (mean±SEM, *p=0.011). (F) Proliferation of purified primary PDA cells in the presence or absence of TGFβ in vitro. Data points represent mean±SEM. (G) Immunoblots of lysates from primary KPD and KP carcinoma cells for ppRB$^{ser780}$, Ccnd1 and p21 expression; Gapdh and Actin were used as loading controls for the respective blots. Normalized p21 expression values were 0.7±0.02 in KP and 0.35±0.27 in KPD carcinoma cells (mean±SD). Scale bars, 50 µm.

FIGS. 5A-5H show how Dpc4 status affects morphological and cellular behaviors associated with metastasis. (A and B) Immunofluorescence staining of actin stress fibers (A) and surface E-cadherin expression (B) in representative KP and KPD cells in the presence or absence of TGFβ. Nuclei are counterstained with DAPI. (C) Scratch wound migration assays of KP and KPD primary carcinoma cells in the presence or absence of TGFβ. (D) Migration assays of scrambled (Scr) or shDpc4-transfected KP and KPD primary carcinoma cells in the presence or absence of TGFβ. (E and F) Loss of Dpc4 in metastatic PDA cells (arrowheads) in the liver, with retention of expression in adjacent hepatocytes (arrows). An isolated metastatic cell (white arrowhead) is also seen amidst hepatic parenchyma (h). (G) Focal loss of nuclear Dpc4 in invasive KPD PDA cells (arrowheads) with retention of expression in adjacent preinvasive (PanIN) lesions (arrow). (H) Focal loss of nuclear Dpc4 in another example of invasive KPD PDA (arrowheads). Scale bars, 50 µm.

FIGS. 6A-6H show the epithelial to mesenchymal transition (EMT) and the metastatic potential of KPD and KP cells. (A) Immunofluorescence of actin stress fibers in representative KP and KPD cells in the presence or absence of TGFβ. Nuclei are counterstained with DAPI. (B) Immunofluorescence of E-cadherin expression in representative KP and KPD cells in the presence or absence of TGFβ. Nuclei are counterstained with DAPI. (C) Scratch wound migration assays for KP and KPD cells in the presence or absence of TGF. (D) Immunoblots after stable knockdown of Dpc4 in KP and KPD carcinoma cells. Gapdh was used as a loading control. (E and F) Immunofluorescence of actin stress fibers in scrambled (Scr) and shDpc4-transfected KP (E) and KPD (F) carcinoma cells in the presence or absence of TGFβ. Nuclei are counterstained with DAPI. (G) Migration of scrambled (Scr) and shDpc4-transfected KP and KPD carcinoma cells in the presence or absence of TGFβ. (H) Representative H&E sections of lungs from mice injected by tail vein with murine KP or KPD PDA cells (n=3 each). Scale bars, 50 µm.

FIGS. 7A-7H show the identification of Runx3 as metastasis-promoter and the post-translational regulation of Runx3 protein levels. (A) IPA analysis of TGFβ pathway array data. (B) Immunoblots for Runx3 in nuclear and cytoplasmic extracts from KP and KPD cells. Gapdh and Parp were used as cytoplasmic (C) and nuclear (N) markers, respectively. (C) Stable expression of murine Flag-Runx3 in two distinct KPD cell lines. Expression was confirmed by immunoblotting with both Flag and Runx3 specific antibodies. (D) The murine Runx3 promoter contains five putative Runx3 binding sites (Runx3) at −1120, −1027, −962, −593 and −585 bp, respectively, from the transcription start site. The promoter also has two canonical SMAD binding elements (SBE). (E) Immunoprecipitation (IP) with anti-Smad2 antibody followed by specific immunoblotting (IB) for indicated proteins on lysates prepared from KP#1 and KPD#1 PDA cells. Cells were incubated in the presence or absence of TGF prior to lysis. IP with IgG was performed as control. (F) qRT-PCR analysis of Hdac5 in KPD and KP cells (*p<0.035). Expression was normalized to preinvasive ductal cells. (G) Immunoblots for Mdm2 in KPD and KP cells. Actin, loading control. (H) Immunoblots for Runx3 in KPD and KP cells treated with Trichostatin A (TSA) at the indicated concentrations. Gapdh, loading control.

Figure 8:
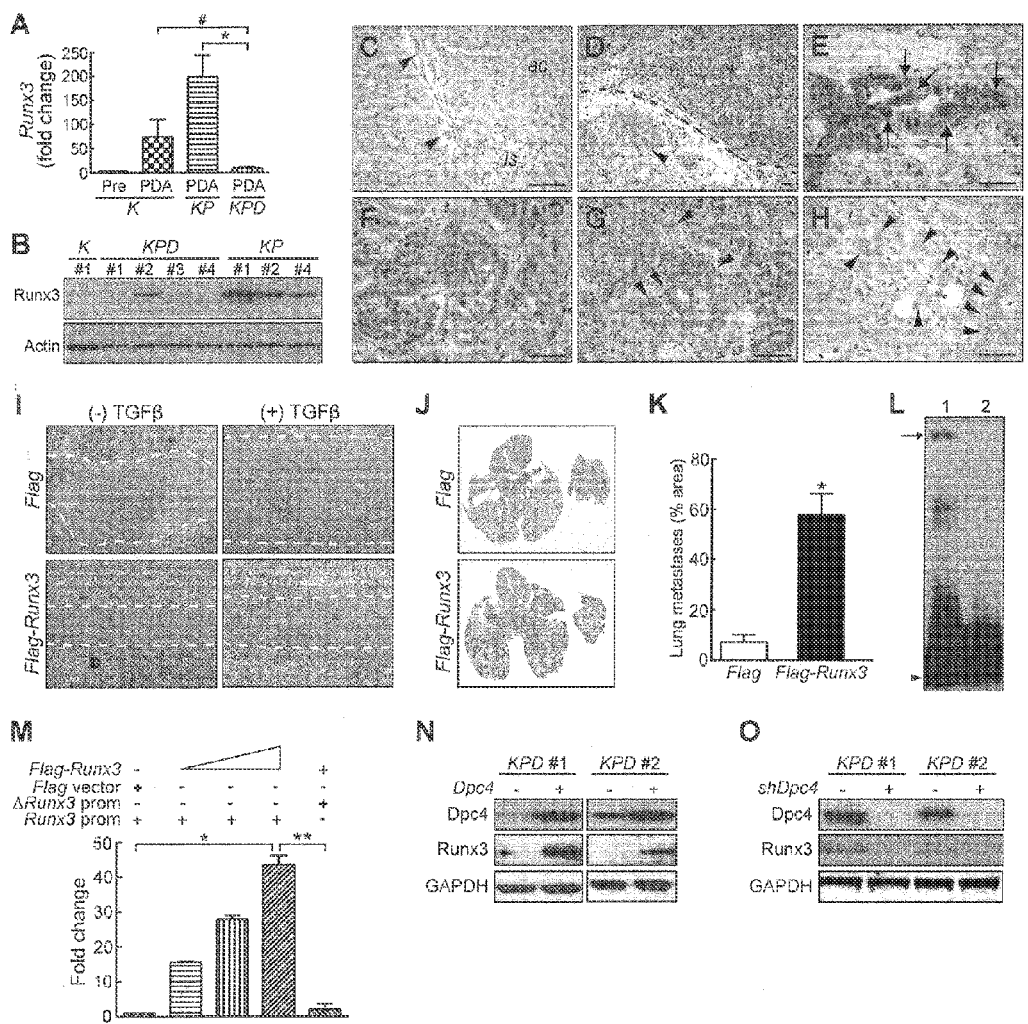

FIGS. 8A-8O shows how Runx3 promotes metastasis in murine PDA. (A) qRT-PCR analyses of relative transcript levels of Runx3 in preinvasive (pre) and invasive (PDA) ductal carcinoma cells (n=3 each, *p=0.025, #p=0.045). (B) Immunoblots for Runx3 in preinvasive K cells and KP and KPD invasive PDA cells. Actin was used as loading control. (C) Runx3 IHC in wild type pancreas. Arrowheads, duct; ac, acinar cells; is, islet cells. (D) Intense nuclear Runx3 expression is seen in KP PDA (asterisk) with faint cytoplasmic expression appreciable in adjacent PanINs (arrowhead). (E and F) Additional examples of nuclear Runx3 staining (arrows) in PDA from KP animals. (G and H) Representative sections from two different KPD PDAs show absence of nuclear Runx3 (arrowheads) and weak cytoplasmic staining. (I) Scratch wound migration assays of Flag and Flag-Runx3 transfected KPD cells in the presence or absence of TGFβ.

(J) Representative sections of lungs from mice injected by tail vein with KPD#1 cells expressing Flag or Flag-Runx3. (K) Metastatic pulmonary tumor burden in mice injected by tail vein with KPD#1 cells expressing Flag or Flag-Runx3. Two different levels from a total of three injected animals were assessed (means±SEM; *p=0.0048). (L) Electrophoretic Mobility Shift Assay (EMSA) of nuclear extracts incubated with labeled DNA probe containing Runx3 promoter sequences. Lane 1, KP nuclear extract and labeled probe; lane 2, KP nuclear extract, labeled probe and excess unlabeled probe; arrow, mobility shift of biotinylated probe indicating specific binding; arrowhead, free probe. (M) Promoter activity of wild-type and truncated (Δ) Runx3 promoter in HEK293T cells with increasing concentrations of Flag-Runx3 (*p=0.0001; **p=0.0002). (N) Immunoblots for Dpc4 and Runx3 in KPD primary carcinoma cells before (−) and after (+) exogenous overexpression of Dpc4. (O) Immunoblots for Dpc4 and Runx3 in KPD primary carcinoma cells before (−) and after (+) transfection with shDpc4.

FIGS. 9A-9H show that RUNX3 promotes metastasis in human PDA. (A) qRT-PCR analyses of RUNX3 expression in human PDA lines. Fold change normalized to HPDE cells. (B) Scratch wound migration assays of MiaPaCa-2, CFPAC-1 and Panc-1 human PDA cell lines in the presence or absence of TGFβ. (C) Scratch wound migration assay of MiaPaca-2 cells overexpressing RUNX3 in the presence or absence of TGFβ. (D) Scratch wound migration assay of CFPAC-1 cells after knockdown of RUNX3 in the presence or absence of TGFβ. (E) Scratch wound migration assay of Panc-1 cells after knockdown of RUNX3 in the presence or absence of TGFβ. (F) Representative sections of lungs from NOD/SCID animals injected with Flag or Flag-RUNX3 transfected MiaPaCa-2 cells. Arrows, metastases. (G) Representative sections of lungs from NOD/SCID animals injected with Scrambled (Scr) or shRUNX3 transfected Panc-1 cells. Arrows, metastases. (H) Livers in vivo (left panels) and ex vivo (right panels) from NOD/SCID animals injected with shRUNX3 or Scrambled (Scr) transfected Panc-1 cells. Arrows, metastases.

Figure 10:
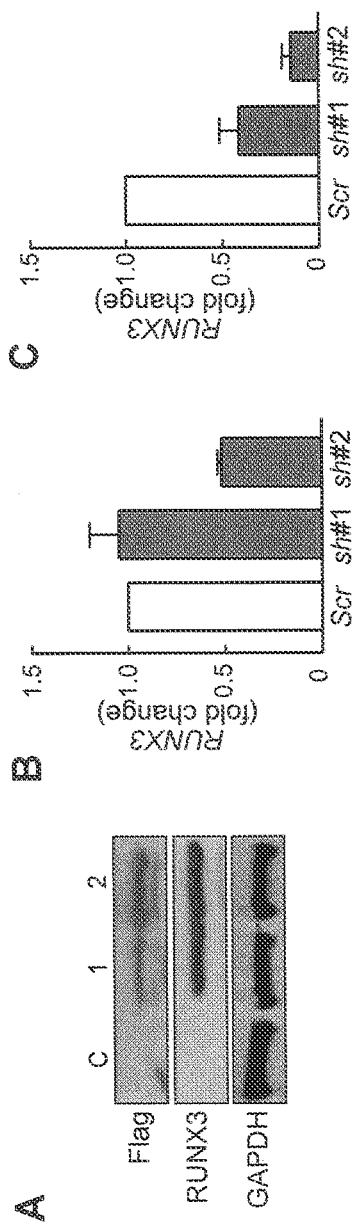
Figure 11A:
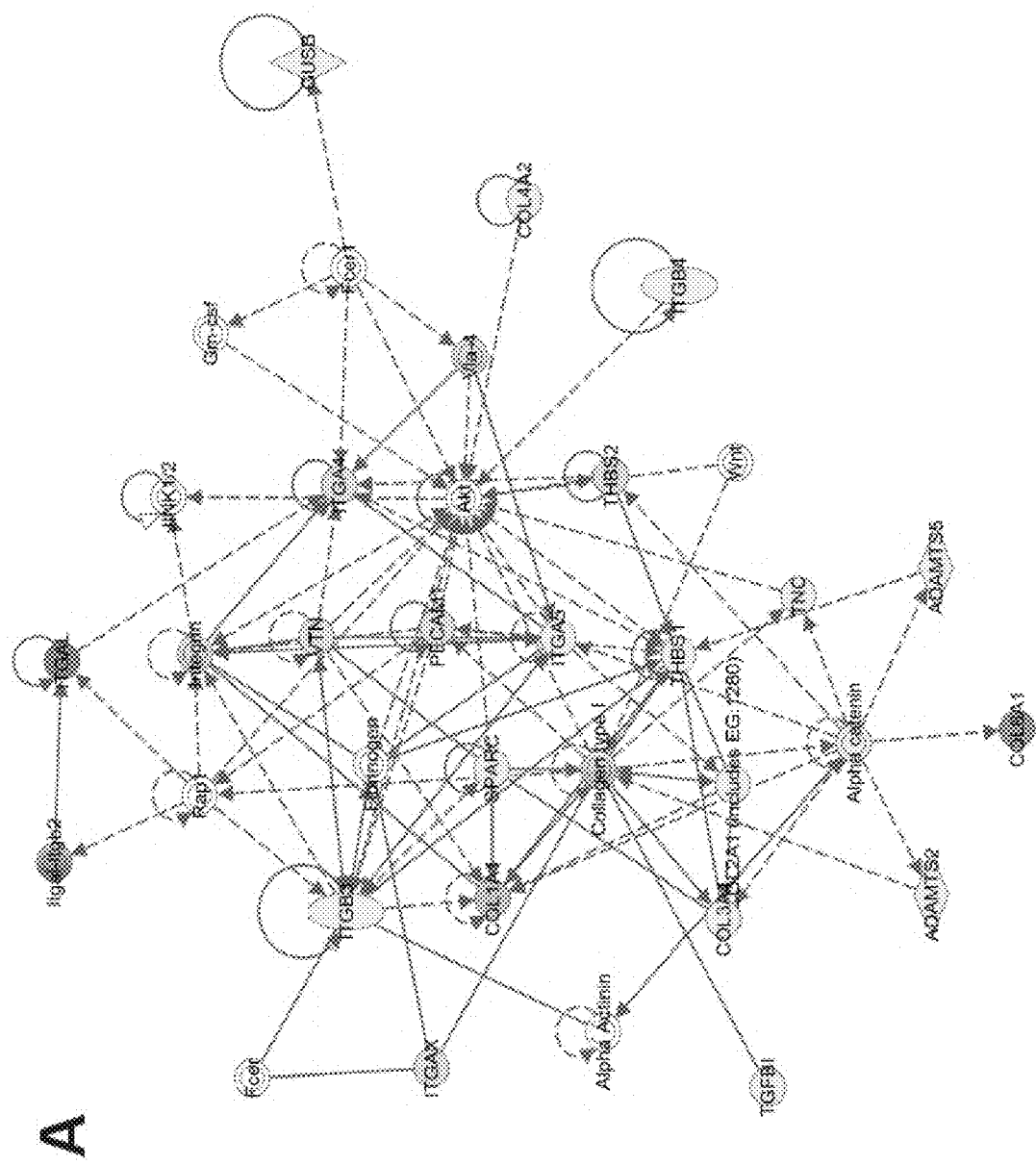
Figures 11B, 11C, 11D:
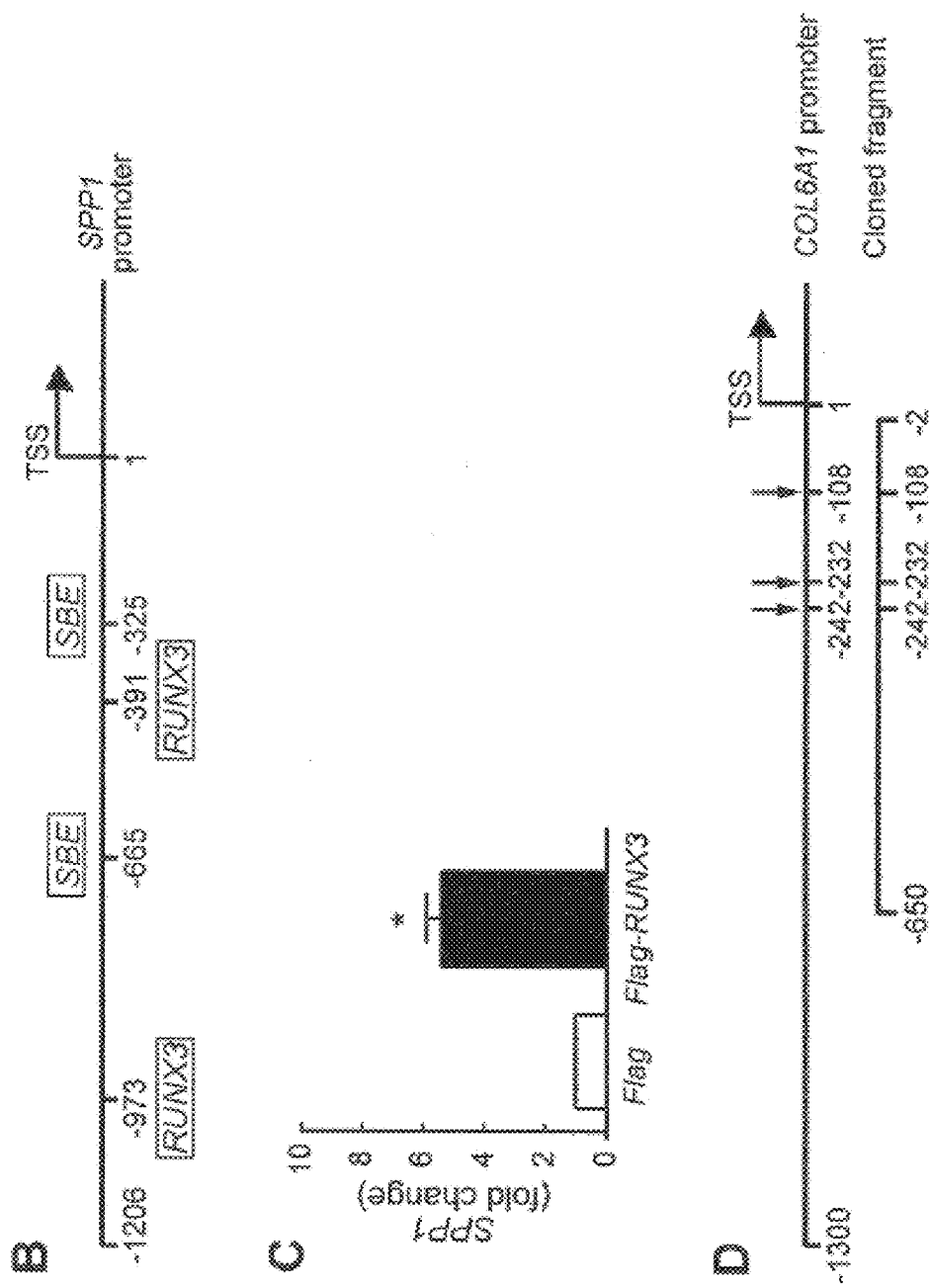

FIGS. 10A-10C show that RUNX3 controls metastasis in human pancreas cancer. (A) Expression of human Flag-RUNX3 in MiaPaCa-2 cells. Expression of the construct in two separate clones (1 and 2) was confirmed by immunoblotting with both Flag- and RUNX3-specific antibodies. GAPDH was used as a loading control. C, control cells. (B) Efficiency of targeted depletion of RUNX3 in CFPAC-1 cells with different RNAi constructs assessed by qRT-PCR. (C) Efficiency of targeted depletion of RUNX3 in Panc-1 cells with different RNAi constructs assessed by qRT-PCR.

FIGS. 11A-11D show that Runx3 promotes metastasis via modulation of ECM components. (A) IPA analysis of differentially regulated ECM pathway genes of in KP and KPD cells. (B) The human SPP1 promoter has two putative RUNX3 binding sites and two SMAD binding elements (SBE). (C) Expression of SPP1 in Flag- and Flag-RUNX3 transfected MiaPaca-2 cells assessed by qRT-PCR (*p=0.0009). (D) The human COL6A1 promoter has three putative RUNX3 binding sites (arrows).

FIGS. 12A-12H show how Runx3 orchestrates the metastasis niche via ECM components. (A) Immunoblots for Col6a1 and Spp1 in three different KP and KPD primary PDA cells. (B) Spp1 transcript levels in Runx3-overexpressing KPD cells as determined by qRT-PCR. *p=0.0016. (C) Immunoblots for Col6a1 and Spp1 in control and Runx3-overexpressing KPD cells. (D) Relative transcript levels in KP, KPD and KPD-Flag-Runx3 carcinoma cells measured by qRT-PCR. Results are normalized against transcript levels in preinvasive K cells (means±SEM, n=3 cell lines for each genotype, *p=0.045, **p=0.0059). (E) Human COL6A1 promoter-luciferase assay in HEK293 cells transfected with Flag or Flag-RUNX3 (*p=0.0024). (F) COL6A1 expression as determined by qRT-PCR in scrambled (Scr) and shRUNX3 (sh#1 and sh#2) transfected Panc-1 cells (*p=0.02). (G) Scratch wound migration assay of control and COL6A1-transfected MiaPaCa-2 cells in the presence or absence of TGFβ. (H) Scratch wound migration assay of KPD cells after over expression of Col6a1 in the presence or absence of TGFβ.

DETAILED DESCRIPTION

The instant disclosure provides methods for treating pancreatic cancer or for reducing the risk of pancreatic cancer or pancreatic cancer metastasis by administering to a patient an inhibitor of RUNX3. A RUNX3 inhibitor may function at the transcriptional level, translational level, or post-translational level. For example, a RUNX3 inhibitor may reduce or block expression of a nucleic acid molecule encoding RUNX3 (e.g., alters transcription factor function, alters promoter function), or the inhibitor may reduce the level of or enhance the degradation of a RUNX3 RNA transcript (e.g., antisense RNA, small interfering RNA). In another example, a RUNX3 inhibitor may block the translation of a RUNX3 mRNA. In a further example, a RUNX3 inhibitor may enhance deacetylation, ubiquitination, or both of RUNX3 by activating, for example, Hdac5, Mdm2, or both.

Also provided herein are inhibitors of RUNX3 for use in treating pancreatic cancer, treating metastasized pancreatic cancer, reducing the risk of pancreatic cancer, or reducing the risk of pancreatic cancer metastasis by administering such compounds or compositions to a patient in need thereof.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

"Inhibit" as used herein refers to an alteration, reduction or abrogation, directly or indirectly, in the expression of a target gene or in the activity of a target molecule (e.g., RUNX3) relative to a control that is statistically, biologically, or clinically significant.

The "percent identity" or "sequence identity," as used herein, refers to the percentage of nucleic acid or amino acid residues in one sequence that are identical with the nucleic acid or amino acid residues in a reference polynucleotide or polypeptide sequence, respectively, (i.e., % identity=number of identical positions/total number of positions×100) after aligning the sequences and introducing gaps, if necessary, to achieve the maximum percent sequence identity of two or more sequences. For proteins, conservative substitutions are not considered as part of the sequence identity. The comparison of sequences and determination of percent identity between two or more sequences is accomplished using a mathematical algorithm, such as BLAST and Gapped BLAST programs at their default parameters (e.g., Altschul et al., *J. Mol. Biol.* 215:403, 1990; Altschul et al., *Nucleic Acids Res.* 25:3389, 1997; see also BLASTN or BLASTP at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8).

As used herein, "ribonucleic acid" or "RNA" means a nucleic acid molecule comprising at least one ribonucleotide molecule. It should be understood that "ribonucleotide" refers to a nucleotide with a hydroxyl group at the 2'-position of a β-D-ribofuranose moiety. The term RNA includes double-stranded (ds) RNA, single-stranded (ss) RNA, isolated RNA (such as partially purified RNA, essentially pure RNA, synthetic RNA, recombinantly produced RNA), altered RNA (which differs from naturally occurring RNA by the addition, deletion, substitution or alteration of one or more nucleotides), or any combination thereof. For example, such altered RNA can include addition of non-nucleotide material, such as at one or both ends of an RNA molecule, internally at one or more nucleotides of the RNA, or any combination thereof. Nucleotides in RNA molecules of the instant disclosure can also comprise non-standard nucleotides, such as naturally occurring nucleotides, non-naturally occurring nucleotides, chemically-modified nucleotides, deoxynucleotides, or any combination thereof. These altered RNAs may be referred to as derivatives or analogs of RNA containing standard nucleotides (i.e., standard nucleotides, as used herein, are considered to be adenine, cytidine, guanidine, thymidine, and uridine).

The term "dsRNA" as used herein refers to any nucleic acid molecule comprising at least one ribonucleotide and is capable of inhibiting or down regulating gene expression, for example, by promoting RNA interference ("RNAi") or gene silencing in a sequence-specific manner. The dsRNAs of the instant disclosure may be suitable substrates for Dicer or for association with RISC to mediate gene silencing by RNAi. One or both strands of the dsRNA can further comprise a terminal phosphate group, such as a 5'-phosphate or 5',3'-diphosphate. As used herein, dsRNA molecules, in addition to at least one ribonucleotide, can further include substitutions, chemically-modified nucleotides, or non-nucleotides. In certain embodiments, dsRNA molecules comprise ribonucleotides up to about 100% of the nucleotide positions.

In addition, as used herein, the term dsRNA is meant to be equivalent to other terms used to describe nucleic acid molecules that are capable of mediating sequence specific RNAi, for example, nicked dsRNA (ndsRNA), gapped dsRNA (gdsRNA), short interfering nucleic acid (siNA), siRNA, micro-RNA (miRNA), short hairpin RNA (shRNA), short interfering oligonucleotide, short interfering substituted oligonucleotide, short interfering modified oligonucleotide, chemically-modified dsRNA, post-transcriptional gene silencing RNA (ptgsRNA), or the like. The term "large double-stranded (ds) RNA" refers to any double-stranded RNA longer than about 40 base pairs (bp) to about 100 bp or more, particularly up to about 300 bp to about 500 bp. The sequence of a large dsRNA may represent a segment of an mRNA or an entire mRNA. A double-stranded structure may be formed by self-complementary nucleic acid molecule or by annealing of two or more distinct complementary nucleic acid molecule strands.

In one aspect, a dsRNA comprises two separate oligonucleotides, comprising a first strand (antisense) and a second strand (sense), wherein the antisense and sense strands are self-complementary (i.e., each strand comprises a nucleotide sequence that is complementary to a nucleotide sequence in the other strand and the two separate strands form a duplex or double-stranded structure, for example, wherein the double-stranded region is about 15 to about 24 or 25 base pairs or about 25 or 26 to about 40 base pairs); the antisense strand comprises a nucleotide sequence that is complementary to a nucleotide sequence of a target nucleic acid molecule or a portion thereof (e.g., RUNX3); and the sense strand comprises a nucleotide sequence corresponding (i.e., homologous) to the target nucleic acid sequence or a portion thereof (e.g., a sense strand of about 15 to about 25 nucleotides or about 26 to about 40 nucleotides corresponds to the target nucleic acid or a portion thereof).

A dsRNA or large dsRNA may include a substitution or modification in which the substitution or modification may be in a phosphate backbone bond, a sugar, a base, or a nucleoside. Such nucleoside substitutions can include natural non-standard nucleosides (e.g., 5-methyluridine or 5-methylcytidine or a 2-thioribothymidine), and such backbone, sugar, or nucleoside modifications can include an alkyl or heteroatom substitution or addition, such as a methyl, alkoxyalkyl, halogen, nitrogen or sulfur, or other modifications known in the art.

As used herein, the term "RNAi" is meant to be equivalent to other terms used to describe sequence specific RNA interference, such as post transcriptional gene silencing, translational inhibition, or epigenetics. For example, dsRNA and single stranded antisense molecules of this disclosure can be used to epigenetically silence genes at the post-transcriptional level, the pre-transcriptional level, or any combination thereof.

As used herein, "gene silencing" refers to a partial or complete loss-of-function through targeted inhibition of gene expression in a cell, which may also be referred to as RNAi "knockdown," "inhibition," "down-regulation," or "reduction" of expression of a target gene. Depending on the circumstances and the biological problem to be addressed, it may be preferable to partially reduce gene expression. Alternatively, it might be desirable to reduce gene expression as much as possible. The extent of silencing may be determined by methods described herein and known in the art, some of which are summarized in PCT Publication No. WO 99/32619. Depending on the assay, quantification of gene expression permits detection of various amounts of inhibition that may be desired in certain embodiments of this disclosure, including prophylactic and therapeutic methods, which will be capable of knocking down target gene expression, in terms of mRNA level or protein level or activity, for example, by equal to or greater than 10%, 30%, 50%, 75% 90%, 95% or 99% of baseline (i.e., normal) or other control levels, including elevated expression levels as may be associated with particular disease states or other conditions targeted for therapy.

As used herein, "target nucleic acid molecule" refers to any nucleic acid molecule whose expression or activity is to be altered (e.g., RUNX3). A target nucleic acid can be DNA, RNA, or derivatives or analogs thereof, and includes single, double, and multi-stranded forms. By "target site" or "target sequence" is meant a sequence within a target nucleic acid molecule (e.g., RUNX3 mRNA) that is "targeted" for cleavage by RNAi and mediated by a dsRNA construct of this disclosure containing a sequence within the antisense strand that is complementary to the target site or sequence.

By "sense region" or "sense strand" is meant one or more nucleotide sequences of a dsRNA molecule having complementarity to one or more antisense regions of the dsRNA molecule. In addition, the sense region of a dsRNA molecule comprises a nucleic acid sequence having homology or identity to a target sequence. By "antisense region" or "antisense strand" is meant a nucleotide sequence of a dsRNA molecule having complementarity to a target nucleic acid sequence. In addition, the antisense region of a dsRNA molecule can comprise a nucleic acid sequence regions having complementarity to one or more sense strands of a dsRNA molecule.

Furthermore, one or more dsRNA may be used to knockdown expression of a target mRNA or a related mRNA splice variant. In this regard, it is noted that a target gene may be transcribed into two or more mRNA splice variants. In certain embodiments, knockdown of one target mRNA splice variant without affecting one or more other target mRNA splice variants may be desired, or vice versa. Alternatively, knockdown of all transcription products of one or more target family genes is contemplated herein.

As used herein, "off-target effect" or "off-target profile" refers to the observed altered expression pattern of one or more genes in a cell or other biological sample not targeted, directly or indirectly, for gene silencing by a dsRNA. For example, an off-target effect can be quantified by using a DNA microarray to determine how many non-target genes have an expression level altered by at least 2-fold or more in the presence of a candidate dsRNA, or derivative or analog thereof specific for a target sequence, such as one or more RUNX3 mRNA. A "minimal off-target effect" means that a dsRNA affects expression by about 2-fold or more of about 25% to about 1% of the non-target genes examined or it means that the off-target effect of substituted or modified dsRNA (e.g., having at least one uridine substituted with a 5-methyluridine or 2-thioribothymidine and optionally having at least one nucleotide modified at the 2'-position), is reduced by at least about 1% to about 80% or more as compared to the effect on non-target genes of an unsubstituted or unmodified dsRNA.

"Analog" as used herein refers to a compound that is structurally similar to a parent compound, but differs slightly in composition (e.g., one atom or functional group is different, added, or removed). An analog may or may not have different chemical or physical properties than the original compound and may or may not have improved biological or chemical activity. For example, an analog may be more hydrophilic or it may have altered activity as compared to a parent compound. An analog may mimic the chemical or biological activity of the parent compound (i.e., it may have similar or identical activity), or, in some cases, may have increased or decreased activity. In other cases, the changes in an analog may impart certain desirable properties (e.g., improved stability, improved bioavailability, improved hydrophilicity, minimized off-target effects, minimized toxicity). An analog may be a naturally or non-naturally occurring (e.g., chemically-modified or recombinant) variant of the original compound. An example of an analog is a mutein (i.e., a protein analog in which at least one amino acid is deleted, added, or substituted with another amino acid). An example of an RNA analog is an RNA molecule having a non-standard nucleotide, such as 5-methyuridine or 5-methylcytidine or 2-thioribothymidine. Other types of analogues include isomers (enantiomers, diastereomers, or the like) and other types of chiral variants of a compound, as well as structural isomers. An analog may be a branched or cyclic variant of a linear compound.

As used herein, the term "derivative" refers to a modification of a compound by chemical or biological means, with or without an enzyme, which modified compound is structurally similar to a parent compound and (actually or theoretically) derivable from that parent compound. Generally, a "derivative" differs from an "analog" in that a parent compound may be the starting material to generate a "derivative," whereas the parent compound may not necessarily be used as the starting material to generate an "analog." A derivative may have different chemical, biological or physical properties of the parent compound, such as being more hydrophilic or having altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include glycosylation, alkylation, acylation, acetylation, ubiqutination, esterification, and amidation.

The term "derivative" also refers to all solvates, for example hydrates or adducts (e.g., adducts with alcohols), active metabolites, and salts of the parent compound. The type of salt that may be prepared depends on the nature of the moieties within the compound. For example, acidic groups such as carboxylic acid groups can form alkali metal salts or alkaline earth metal salts (e.g., sodium salts, potassium salts, magnesium salts and calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts, for example, with inorganic acids such as hydrochloric acid, sulfuric acid or phosphoric acid, or with organic carboxylic acids and sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

Other types of derivatives include conjugates and prodrugs of a parent compound (i.e., chemically modified derivatives which can be converted into the original compound under physiological conditions). For example, the prodrug may be an inactive form of an active agent. Under physiological conditions, the prodrug may be converted into the active form of the compound. Prodrugs may be formed, for example, by replacing one or two hydrogen atoms on nitrogen atoms by an acyl group (acyl prodrugs) or a carbamate group (carbamate prodrugs). More detailed information relating to prodrugs may be found in, for example, Fleisher et al., *Adv. Drug Del. Rev* 19:115, 1996; Design of Prodrugs, H. Bundgaard (ed.), Elsevier, 1985; or Bundgaard, *Drugs of the Future* 16:443, 1991.

The term "pyrimidine" as used herein refers to conventional pyrimidine bases, including standard pyrimidine bases uracil and cytosine. In addition, the term pyrimidine is contemplated to embrace natural non-standard pyrimidine bases or acids, such as 5-methyluracil, 2-thio-5-methyluracil, 4-thiouracil, pseudouracil, dihydrouracil, orotate, 5-methylcytosine, or the like, as well as a chemically-modified bases or "universal bases," which can be used to substitute for a standard pyrimidine within nucleic acid molecules of this disclosure.

The term "purine" as used herein refers to conventional purine bases, including standard purine bases adenine and guanine. In addition, the term purine is contemplated to embrace natural non-standard purine bases or acids, such as N2-methylguanine, inosine, or the like, as well as a chemically-modified bases or "universal bases," which can be used to substitute for a standard purine within nucleic acid molecules of this disclosure.

As used herein, the term "universal base" refers to nucleotide base analogs that form base pairs with each of the standard DNA/RNA bases with little discrimination between them, and is recognized by intracellular enzymes (see, e.g., Loakes et al., *J. Mol. Bio.* 270:426, 1997). Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, e.g., Loakes, *Nucleic Acids Res.* 29:2437, 2001).

As used herein, the term "isolated" means that the molecule referred to is removed from its original environment, such as being separated from some or all of the co-existing materials in a natural environment (e.g., a natural environment may be a cell).

The term "biological sample" includes a blood sample, biopsy specimen, tissue explant, organ culture, biological fluid (e.g., serum, urine, CSF) or any other tissue or cell or other preparation from a subject or a biological source. A subject or biological source may, for example, be a human or non-human animal, a primary cell culture or culture adapted cell line including genetically engineered cell lines that may contain chromosomally integrated or episomal recombinant nucleic acid molecules, somatic cell hybrid cell lines, immortalized or immortalizable cell lines, differentiated or differentiatable cell lines, transformed cell lines, or the like.

In further embodiments of this disclosure, a subject or biological source may be suspected of having or being at risk for having a disease, disorder or condition, including a malignant disease, disorder or condition (e.g., pancreatic cancer). In certain embodiments, a subject or biological source may be suspected of having or being at risk for having a hyperproliferative disease (e.g., pancreatic cancer), and in certain other embodiments of this disclosure the subject or biological source may be known to be free of a risk or presence of such disease, disorder, or condition.

By "subject" is meant an organism, which may be a donor or recipient of explanted cells, or the cells themselves. "Subject" also refers to an organism to which a small molecule, chemical entity, nucleic acid molecule, peptide or polypeptide of this disclosure can be administered to inhibit RUNX3. In one embodiment, a subject is a mammal or mammalian cell. In another embodiment, a subject is a human or human cell.

"Treatment," "treating" or "ameliorating" refers to either a therapeutic treatment or prophylactic/preventative treatment. A treatment is therapeutic if at least one symptom of disease (e.g., pancreatic cancer) in an individual receiving treatment improves or a treatment may delay worsening of a progressive disease in an individual, or prevent onset of additional associated diseases (e.g., metastases from pancreatic cancer).

A "therapeutically effective amount (or dose)" or "effective amount (or dose)" of a RUNX3 inhibitor refers to that amount of compound sufficient to result in amelioration of one or more symptoms of the disease being treated (e.g., pancreatic cancer) in a statistically significant manner. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or in separate formulations).

The term "pharmaceutically acceptable" refers to molecular entities and compositions that do not produce allergic or other serious adverse reactions when administered using routes well known in the art.

A "patient in need" or "subject in need" refers to a patient or subject at risk of, or suffering from, a disease, disorder or condition (e.g., pancreatic cancer) that is amenable to treatment or amelioration with a RUNX3 inhibitor or a composition thereof, as provided herein.

In certain embodiments, provided are compounds for reducing the risk of or treating pancreatic cancer or metastatic pancreatic cancer include inhibitors of RUNX3 expression, such as small molecules, chemical entities, nucleic acid molecules, peptides or polypeptides. In particular embodiments, the RUNX3 inhibitor is a dsRNA (interfering RNA) or antisense RNA. In certain further embodiments, the RUNX3 inhibitor comprises an isolated nucleic acid molecule with the sequence set forth in SEQ ID NO.: 20.

In certain further embodiments, provided are methods for reducing the risk of or treating pancreatic cancer, comprising administering to a subject in need thereof an inhibitor of RUNX3 expression or activity, such as a small molecule, chemical entity, nucleic acid molecule, peptide or polypeptide. In particular embodiments, the RUNX3 inhibitor is a dsRNA (interfering RNA) or antisense RNA. In certain further embodiments, the RUNX3 inhibitor comprises an isolated nucleic acid molecule with the sequence set forth in SEQ ID NO.: 20.

By way of background, Runx3 belongs to a family of transcription factors involved in development and differentiation (Ito, *Adv. Cancer Res.* 99:33, 2008; Speck et al., *Cancer Res.* 59:1789s, 1999) and whose best characterized members are Runx1 and Runx2. The specificity of the upregulation in Runx3 in KP cells was underscored by the lack of significant changes in these close family members (−1.2-fold for Runx1 and 1.5-fold for Runx2; not shown). RUNX1 and RUNX2 have been identified as tumor suppressor genes (TSGs) in hematopoietic malignancies (Blyth et al., *Nat. Rev. Cancer* 5:376, 2005). Its alternate designation of AML2 notwithstanding, what little is known about the role of RUNX3 in malignancy comes primarily from studies of solid tumors, where it has been implicated on both sides of the cancer divide, and sometimes with contradicting conclusions in the same cancer.

Several studies point toward a tumor suppressive role for RUNX3 (e.g., Bae and Choi, *Oncogene* 23:4336, 2004), but a small number of reports indicate that it has oncogenic potential and that this potential might extend beyond murine lymphomas (Debernardi et al., *Genes Chromosomes Cancer* 37:149, 2003; Lacayo et al., *Blood* 104:2646, 2004). For instance, RUNX3 overexpression has been reported in basal cell (Salto-Tellez et al., *Oncogene* 25:7646, 2006), skin (Lee et al., *Clin. Exp. Dermatol.* 36:769, 2011 b), head and neck (Tsunematsu et al., *PLoS One* 4:e5892, 2009) and ovarian cancers (Lee et al., *Gynecol. Oncol.* 122:410, 2011a). Finally, in gastric carcinoma, RUNX3 has been separately identified as either a TSG by some groups (e.g., Li et al., 2002) or an oncogene by others (e.g., Levanon et al., 2011). Indeed, its specific role in tumorigenesis remains the subject of considerable controversy (see, also, Ito et al., *Oncogene* 28, 1379, 2009; Levanon et al., *EMBO Mol. Med.* 3:593, 2011; Levanon et al., *Mech. Dev.* 109:413, 2001; Li et al., Cell 109:113, 2002 and see below).

Pancreatic ductal adenocarcinoma (PDA) is notorious for its extreme penchant for metastatic spread. The chronological sequence in which cardinal mutations in KRAS, P53 and SMAD4/DPC4 occur can define the histopathology and metastatic potential of the resultant PDAs. For the first, the present disclosure teaches that heterozygous mutation of Smad4/Dpc4 early in the progression of precursor lesions expressing Kras$^{G12D}$ and Trp53$^{R172H}$ shifts the disease burden toward increased primary tumor growth while almost completely abolishing distant metastases. Conversely, data provided herein shows that heterozygous Dpc4 mutation late in progression further augments inherently prolific metastasis. Unexpectedly, it was found that this switch governing the balance between proliferation and dissemination is regulated by the transcription factor, RUNX3, which orchestrates a coherent metastatic program that both drives cell migration and remodels the nascent metastatic niche.

While not wishing to be bound by theory, RUNX3 might orchestrate a coordinated program that shifts the pancreatic cancer cell's priorities from proliferation to dissemination and metastatic colonization of distant sites. Overcoming the barriers to successful metastasis requires achieving a migratory capability, as well as the ability to refashion the extra cellular matrix (ECM) and microenvironment to support growth in a foreign organ. In KPD cells, resting levels of Runx3 are kept tightly in check via coordinated Mdm2-and Hdac5-mediated protein degradation, together with relatively low levels of transcriptional initiation because of decreased Runx3/Smad4 complex formation. In KP cells, however, Mdm2 and Hdac5 are both relatively low, allowing basal levels of Runx3 protein to reach a threshold at which point transcription is further rapidly increased by positive feedback of Runx3 on its own promoter. Elevated levels of Runx3 activate the "metastatic switch," increasing cell cycle checkpoint gene expression and expression, along with secretion of proteins that support and promote migration and colonization. In this manner, RUNX3 helps regulate a cell fate decision node between the competing demands of local growth and invasion on the one hand, and dissemination and metastatic colonization on the other. In shifting cellular resources from proliferation to colonization, RUNX3 drives cells to refashion their microenvironment to overcome the biologic barriers to establishing a metastatic foothold.

In further embodiments, provided are methods for reducing the risk of or treating pancreatic cancer, comprising administering to a subject in need thereof a compound capable of blocking the association of RUNX3 with a second transcription factor, such as SMAD4 or a complex of SMAD4 with SMAD2. In further embodiments, provided are methods for reducing the risk of or treating pancreatic cancer, comprising administering to a subject in need thereof an agent that enhances deacetylation of RUNX3, such as an activator of HDAC5 activity (preferably a pancreas-specific activator of HDAC5, such as increasing expression via gene therapy). In still further embodiments, provided are methods for reducing the risk of or treating pancreatic cancer, comprising administering to a subject in need thereof an agent that enhances ubiquitination of RUNX3, such as an activator of HDAC5 activity (preferably a pancreas-specific activator of HDAC5), an activator of MDM2 activity (preferably a pancreas-specific activator of MDM2), or a combination thereof. In further embodiments, the methods further comprise administering an expression or activity inhibitor of a cyclin D (such as cyclin D1), a cyclin E, or a combination thereof.

In yet other embodiments, provided are methods for reducing the risk of or treating metastasized pancreatic cancer, comprising administering to a subject in need thereof an inhibitor of RUNX3 expression or activity, such as a small molecule, chemical entity, nucleic acid molecule, peptide or polypeptide. In particular embodiments, the RUNX3 inhibitor is a dsRNA (interfering RNA) or antisense RNA. In certain further embodiments, the RUNX3 inhibitor comprises an isolated nucleic acid molecule with the sequence set forth in SEQ ID NO.: 20.

In still further embodiments, provided are methods for reducing the risk of or treating a pancreatic cancer precursor lesion, comprising administering to a subject in need thereof an inhibitor of RUNX3 expression or activity, such as a small molecule, chemical entity, nucleic acid molecule, peptide or polypeptide. In particular embodiments, the RUNX3 inhibitor is a dsRNA (interfering RNA) or antisense RNA. In certain further embodiments, the RUNX3 inhibitor comprises an isolated nucleic acid molecule with the sequence set forth in SEQ ID NO.: 20.

In certain further embodiments, provided are methods for reducing the risk of or treating a metastatic niche associated with pancreatic cancer, comprising administering to a subject in need thereof an inhibitor of RUNX3 expression or activity, such as a small molecule, chemical entity, nucleic acid molecule, peptide or polypeptide. In particular embodiments, the RUNX3 inhibitor is a dsRNA (interfering RNA) or antisense RNA. In certain further embodiments, the RUNX3 inhibitor comprises an isolated nucleic acid molecule with the sequence set forth in SEQ ID NO.: 20.

Within additional aspects of this disclosure, combination formulations and methods are provided comprising an effective amount of RUNX3 inhibitor of the present disclosure in combination with one or more secondary or adjunctive therapies. Such therapies may be additional active agents that are formulated together or administered coordinately with the RUNX3 inhibitors of this disclosure to control pancreatic cancer or associated condition, as described herein. Useful adjunctive or neoadjunctive therapies for combinatorial formulation or coordinate treatment methods include, for example, enzymatic nucleic acid molecules, allosteric nucleic acid molecules, antisense, decoy, or aptamer nucleic acid molecules, antibodies such as monoclonal antibodies, enzymes (e.g., hyalurodinases), small molecules and other organic or inorganic compounds including metals, salts and ions, steroids, non-steroidal anti-inflammatory drugs (NSAIDs), and other drugs or active agents or procedures indicated for treating pancreatic cancer, including surgery, chemotherapy, radiation therapy, chemoradiation therapy, or the like.

In certain embodiments, any of the aforementioned methods further comprise a second method of treatment, such as surgery, chemotherapy, radiation therapy, or any combination thereof. For pancreatic cancer or a pancreatic cancer precursor lesion, several therapeutic regimens are known in the art. For example, the Whipple procedure, or pancreaticoduodenectomy, is the most commonly performed surgery to remove pancreatic tumors. Pancreatic cancer is considered resectable if the tumor appears to be localized to the pancreas without invasion into important surrounding structures, such as the mesenteric blood vessels (that supply blood to the intestines) located adjacent to the head portion of the pancreas. Furthermore there should be no evidence of metastatic spread to the liver or the intestinal lining. In a standard Whipple operation, a surgeon will remove the head of the pancreas, the gallbladder, part of the duodenum (i.e., the uppermost portion of the small intestine), a small portion of the stomach called the pylorus, and the lymph nodes near the head of the pancreas. Then the remaining pancreas and digestive organs are reconnected so that pancreatic digestive enzymes, bile, and stomach contents will flow into the small intestine during digestion. In another type of Whipple procedure, known as pylorus preserving Whipple, the bottom portion of the stomach, or pylorus, is not removed. In either case, such a surgery can last from about 6 hours to about 10 hours.

When pancreatic cancer has grown beyond the confines of the pancreas to invade surrounding vital structures, such a locally advanced pancreatic cancer is not treated by surgery. Treatment of locally advanced pancreatic cancer includes chemotherapy and radiation therapy. Exemplary chemotherapeutic drugs used for the treatment of pancreatic cancer include 5-fluorouracil, leukovirin, gemcitabine, cisplatin, irinotecan, paclitaxel, nanoparticle albumin bound (nab)-paclitaxel, docetaxel, capecitabine, oxaliplatin, and the FOLFIRINOX combination (5-fluorouracil, leucovorin, irinotecan and oxaliplatin). Exemplary radiation therapy is delivered in daily fractions over a six week period to a total dose of approximately 5,000 rads, which may be external (e.g, high energy X-rays) or internal (e.g., radiation contained in needles, seeds, wires, or catheters, which are placed directly into or near a tumor). In certain embodiments, chemotherapy may be administered together or sequentially with the radiation therapy.

Exemplary chemotherapeutic agents include alkylating agents (e.g., cisplatin, oxaliplatin, carboplatin, busulfan, nitrosoureas, nitrogen mustards, uramustine, temozolomide), antimetabolites (e.g., aminopterin, methotrexate, mercaptopurine, fluorouracil, cytarabine, gemcitabine), taxanes (e.g., paclitaxel, nab-paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., alemtuzumab, bevacizumab, cetuximab, gemtuzumab, panitumumab, rituximab, tositumomab, trastuzumab), vinca alkaloids (e.g., vincristine, vinblastine, vindesine, vinorelbine), cyclophosphamide, prednisone, leucovorin, oxaliplatin, hyalurodinases.

Other exemplary adjunctive or neoadjunctive therapies for use with a RUNX3 inhibitor include expression or activity inhibitors of Bmpr1a, Smad5, Tgfb3, Smad4, Bmp1, Itgb7, Tgfb1i1, Bmper, Ltbp1, Ltbp2, Itgb5, Id1, Tgfbi, Dlx2, or any combination thereof. Still further exemplary adjunctive or neoadjunctive therapies for use with a RUNX3 inhibitor include expression or activity inhibitors of Ctgf, Selp, Timp2, Col5a1, Ncam1, Thbs3, Mmp11, Sgce, Fn1, Vcam1, Ecm1, Adamts1, Mmp2, Thbs1, Fbln1, Tgfbi, Cdh2, Mmp10, Timp3, Spp1, Vcan, Sparc, Col6a1, or any combination thereof. In yet further exemplary adjunctive or neoadjunctive therapies for use with a RUNX3 inhibitor include expression or activity inhibitors of a cyclin D, a cyclin E, or a combination thereof, or in combination with conventional chemotherapies such as gemcitabine, nab-paclitaxel, FOLFIRINOX combination, or any combination thereof. In yet other embodiments, a adjunctive or neoadjunctive therapy for use with a RUNX3 inhibitor includes an agent capable of degrade hyaluronic acid (HA), such as hyaluronidases, a CD44 antagonist, or a combination thereof.

To practice the coordinate administration methods of this disclosure, a RUNX3 inhibitor is administered simultaneously or sequentially in a coordinated treatment protocol with one or more secondary or adjunctive therapies, such as surgery, chemotherapy, radiation therapy, chemoradiation therapy, or the like. The coordinate administration may be done in either order, and there may be a time period while only one or both (or all) therapies, individually or collectively, exert their biological activities. A distinguishing aspect of all such coordinate treatment methods is that a RUNX3 inhibitor present in a composition elicits some favorable clinical response, which may or may not be in conjunction with a secondary clinical response provided by the secondary therapeutic agent. For example, the coordinate administration of a RUNX3 inhibitor with a secondary therapeutic agent as contemplated herein can yield an enhanced (e.g., synergistic) therapeutic response beyond the therapeutic response elicited by either or both a RUNX3 inhibitor or secondary therapeutic agent or procedure alone.

In further embodiments, provided are compositions for reducing the risk of or treating pancreatic cancer or metastatic pancreatic cancer that include an inhibitor of RUNX3 expression (such as small molecules, chemical entities, nucleic acid molecules, peptides or polypeptides) and a pharmaceutically acceptable carrier, diluent or excipient. In certain further embodiments, the composition contains a RUNX3 inhibitor that is a dsRNA (interfering RNA) or antisense RNA. In still further embodiments, the composition contains a RUNX3 inhibitor that is an isolated nucleic acid molecule with the sequence set forth in SEQ ID NO.: 20.

For the purposes of administration, the compounds of the present disclosure may be administered as a raw chemical or may be formulated as pharmaceutical compositions. Pharmaceutical compositions of the present disclosure may comprise a small molecule, chemical entity, nucleic acid molecule, peptide or polypeptide, and a pharmaceutically acceptable carrier, diluent or excipient. The small molecule, chemical entity, nucleic acid molecule, peptide or polypeptide composition will be in an amount that is effective to treat a particular disease or condition of interest—that is, in an amount sufficient for reducing the risk of or treating pancreatic cancer, metastases arising from the pancreatic cancer, a pancreatic cancer precursor lesion, a metastatic niche associated with pancreatic cancer or any of the other associated indication described herein, and preferably with acceptable toxicity to a patient. Compounds for use in the methods described herein can be determined by one skilled in the art, for example, as described in the Examples below. Appropriate concentrations and dosages can be readily determined by one skilled in the art.

Administration of the compounds of this disclosure, or their pharmaceutically acceptable salts, in pure form or in an appropriate pharmaceutical composition, can be carried out using any mode of administration for agents serving similar utilities. The pharmaceutical compositions of this disclosure can be prepared by combining a compound of this disclosure with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include oral, topical, transdermal, inhalation, parenteral, sublingual, buccal, rectal, vaginal, and intranasal.

The term "parenteral" as used herein includes subcutaneous injections, intravenous, intramuscular, intrasternal injection or infusion techniques. Pharmaceutical compositions of this disclosure are formulated to allow the active ingredients contained therein to be bioavailable upon administration of the composition to a patient. Compositions that will be administered to a subject or patient take the form of one or more dosage units, where for example, a tablet may be a single dosage unit, and a container of a compound of this disclosure in aerosol form may hold a plurality of dosage units. Actual methods of preparing such dosage forms are known, or will be apparent, to those skilled in this art (see, e.g., *Remington: The Science and Practice of Pharmacy,* $22^{nd}$ Edition (Pharmaceutical Press, 2012). The composition to be administered will, in any event, contain a therapeutically effective amount of a compound of this disclosure, or a pharmaceutically acceptable salt thereof, for reducing the risk of or treating pancreatic cancer, metastases arising from the pancreatic cancer, a pancreatic cancer precursor lesion, a metastatic niche associated with pancreatic cancer or other condition of interest in accordance with the teachings of this disclosure.

As a solid composition for oral administration, the pharmaceutical composition may be formulated into a powder, granule, compressed tablet, pill, capsule, chewing gum, wafer or the like form. Exemplary solid compositions can contain one or more inert diluents or edible carriers. In addition, one or more additives may be present, including binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; or a coloring agent. When a pharmaceutical composition is in the form of a capsule, such as a gelatin capsule, it may contain, in addition to materials of the above type, a liquid carrier such as polyethylene glycol or oil or combinations thereof.

The pharmaceutical composition may be in the form of a liquid, such as an elixir, syrup, solution, emulsion, or suspension. In certain embodiments, a liquid composition may be formulated for oral administration or for delivery by injection, as two examples. When intended for oral administration, exemplary compositions may further contain, in addition to one or more compounds of this disclosure, a sweetening agent, preservative, dye/colorant, flavor enhancer, or any combination thereof. Exemplary compositions intended for administration by injection may further contain a surfactant, preservative, wetting agent, dispersing agent, suspending agent, buffer, stabilizer, isotonic agent, or any combination thereof.

Liquid pharmaceutical compositions of this disclosure, whether they are solutions, suspensions or other like forms, may further comprise adjuvants, including sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A pharmaceutical composition of this disclosure may be intended for topical administration, in which case the carrier may comprise a suitable solution, emulsion, ointment, gel base, or any combination thereof. The base, for example, may comprise petrolatum, lanolin, polyethylene glycols, bee wax, mineral oil, diluents such as water and alcohol, emulsifiers, stabilizers, or any combination thereof. Thickening agents may be present in a pharmaceutical composition of this disclosure for topical administration. If intended for transdermal administration, the composition may include a transdermal patch or iontophoresis device.

A pharmaceutical composition of this disclosure may be intended for rectal administration, in the form, for example, of a suppository, which will melt in the rectum and release the active compound(s). A composition for rectal administration may contain an oleaginous base as a suitable nonirritating excipient. Exemplary bases include lanolin, cocoa butter, polyethylene glycol, or any combination thereof.

A pharmaceutical composition of this disclosure may include various materials that modify the physical form of a solid or liquid dosage unit. For example, a composition may include materials that form a coating shell around the active ingredient(s). Exemplary materials for forming a coating shell may be inert, such as sugar, shellac, or other enteric coating agents. Alternatively, active ingredient(s) may be encased in a gelatin capsule.

In certain embodiments, compounds and compositions of this disclosure may be in the form of a solid or liquid. Exemplary solid or liquid formulations include semi-solid, semi-liquid, suspension, and gel forms. A pharmaceutical composition of this disclosure in solid or liquid form may further include an agent that binds to the compound of this disclosure and thereby assists in the delivery of the compound. Suitable agents that may act in this capacity include a monoclonal or polyclonal antibody, a protein, or a liposome.

A pharmaceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, and the like, which together may form a kit.

Pharmaceutical compositions of this disclosure may be prepared by methodology well known in the pharmaceutical art. For example, a pharmaceutical composition intended to be administered by injection can be prepared by combining a compound of this disclosure with sterile, distilled water to form a solution. A surfactant may be added to facilitate the formation of a homogeneous solution or suspension. Surfactants are compounds that non-covalently interact with the compound of this disclosure to facilitate dissolution or homogeneous suspension of a compound in an aqueous delivery system.

Compounds of this disclosure, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Following administration of RUNX3 inhibitors according to the formulations and methods of this disclosure, test subjects will exhibit about a 10% up to about a 99% reduction in one or more symptoms associated with the disease or disorder being treated (e.g., pancreas cancer), as compared to placebo-treated or other suitable control subjects.

Compounds of this disclosure, or pharmaceutically acceptable derivatives thereof, may also be administered simultaneously with, prior to, or after administration of one or more other therapeutic agents. Such combination therapy includes administration of a single pharmaceutical dosage formulation which contains a compound of this disclosure and one or more additional active agents, as well as administration of the compound of this disclosure and each active agent in its own separate pharmaceutical dosage formulation. For example, a compound of this disclosure and the other active agent can be administered to the patient together in a single oral dosage composition such as a tablet or capsule, or each agent administered in separate oral dosage formulations. Where separate dosage formulations are used, the compounds of this disclosure and one or more additional active agents can be administered at essentially the same time, i.e., concurrently, or at separately staggered times, i.e., sequentially; combination therapy is understood to include all these regimens.

It will also be appreciated by those skilled in the art that in the process described herein the functional groups of intermediate compounds may need to be protected by suitable protecting groups. Such functional groups include hydroxy, amino, mercapto, and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, or the like. Suitable protecting groups for mercapto include —C(O)—R" (where R" is alkyl, aryl or arylalkyl), p-methoxybenzyl, trityl or the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those of skill in the art, although such protected derivatives of compounds of this disclosure may not possess pharmacological activity as such, they may be administered to a mammal and thereafter metabolized in the body to form compounds of this disclosure which are pharmacologically active. Such derivatives may, therefore, be described as "prodrugs". In certain embodiments, compounds of this disclosure are in the form of a prodrug.

Furthermore, all compounds of this disclosure that exist in free base or acid form can be converted to their pharmaceutically acceptable salts by treatment with the appropriate inorganic or organic base or acid by methods known to those skilled in the art. Salts of the compounds of this disclosure can be converted to their free base or acid form by standard techniques.

EXAMPLES

Example 1

Targeting Conditional Alleles to the Murine Pancreas

Figure 1:
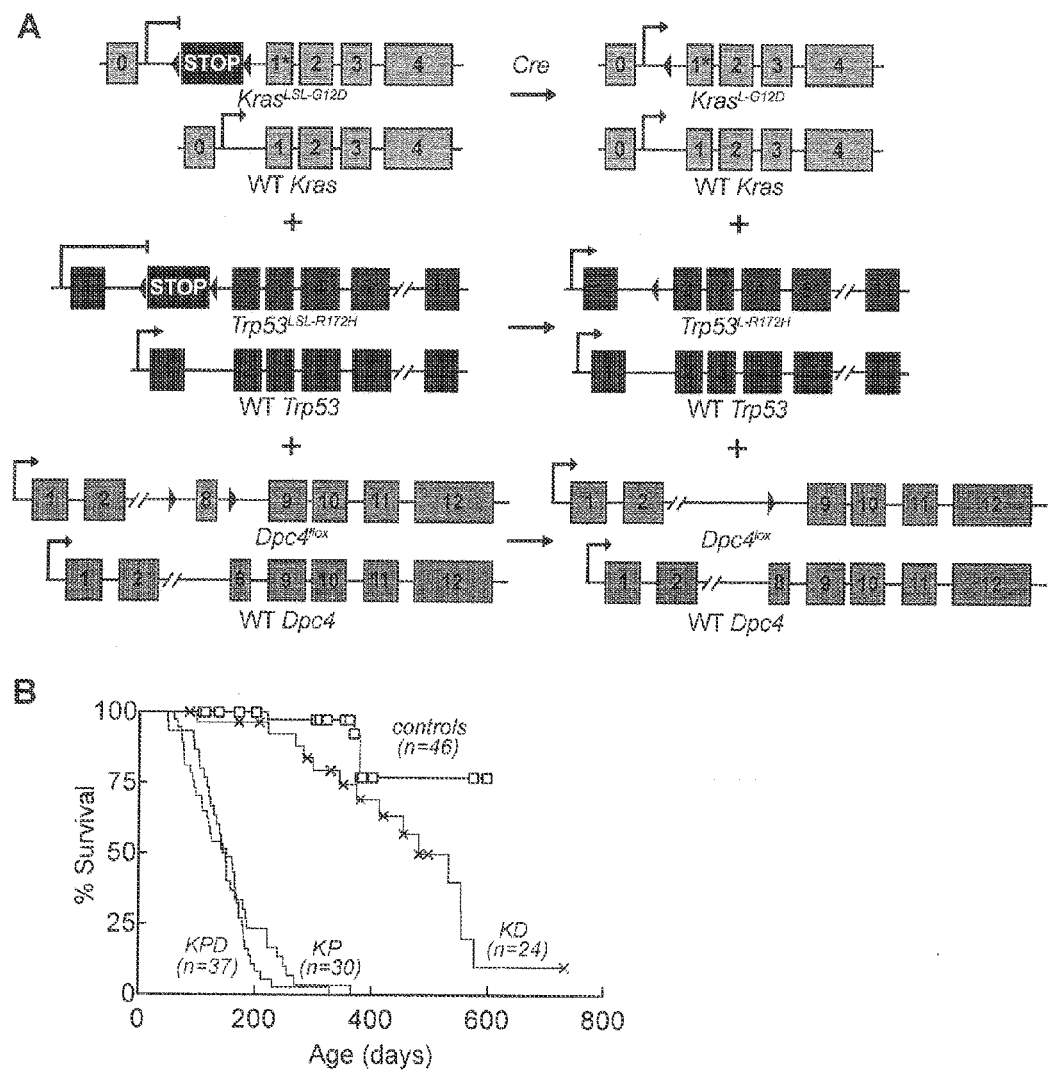
FIGS. 1A and 1B show the effect of targeting endogenous $Kras^{G12D}$ and $Trp53^{R172H}$ expression and deletion of Dpc4 to the murine pancreas. (A) Activation of $Kras^{LSL-G12D/+}$ and $Trp53^{LSL-R172H/+}$ and deletion of endogenous $Dpc4^{flox/+}$ alleles upon pancreas-specific exposure to Cre recombinase ($p48^{cre/+}$) in quadruple mutant $Kras^{LSL-G12D/+}$.

Conditional Trp53$^{LSL-R172H/+}$ (Olive et al., *Cell* 119:847, 2004; Hingorani et al., 2005), Dpc4$^{flox/+}$ (Yang et al., *Genesis* 32:80, 2002), Kras$^{LSL-G12D/+}$ (Hingorani et al., *Cancer Cell* 4:437, 2003; Hingorani et al., 2005; Izeradjene et al., *Cancer Cell* 11:229, 2007), and p48$^{Cre/+}$ (Kawaguchi et al., *Nat. Gen.* 32:128, 2002; Izeradjene et al., 2007) strains were interbred to obtain various multiple mutant animals (FIG. 1A). In particular, the following transgenic mice, along with various littermate control animals, on a mixed B1Swiss/129/SvJae/C57Bl/6 background were generated: (1) Kras$^{LSL-G12D/+}$::Trp53$^{LSL-R172H/+}$::p48$^{Cre/+}$ (KP); (2) Kras$^{LSL-G12D/+}$::Trp53$^{LSL-R172H/+}$::Dpc4$^{flox/+}$::p48$^{Cre/+}$ (KPD); (3) Trp53$^{LSL-R172H/+}$::Dpc4$^{flox/+}$::p48$^{Cre/+}$ (PD); (4) Kras$^{LSL-G12D/+}$::Dpc4$^{flox/+}$::p48$^{Cre/+}$ (KD), and (5) Kras$^{LSL-G12D/+}$::Dpc4$^{flox/flox}$::p48$^{Cre/+}$ (KDD). Nude mice (Athymic NCr-nu/nu, NCI Frederick USA) and NOD.SCID/NCr mice (NOD.SCID Core, FHCRC) were used in pulmonary metastasis assays.

When Cre recombinase is expressed, exon 8 of the floxed Smad4/Dpc4 allele results in a frame-shift, rapid degradation of the transcript, and no evidence of SMAD4/DPC4 protein expression (Izeradjene et al., 2007). For Trp53$^{R172H}$ and Kras$^{G12D}$, the Lox-stop-Lox (LSL) transcription stop sequence is deleted in the presence of Cre recombinase, which leads to expression of the mutant genes.

Histology and Immunohistochemistry

Tissues were fixed in 10% neutral buffered formalin, paraffin embedded and 5 μm sections were prepared. Routine H&E and immunostaining was done as previously described (Hingorani et. al., 2003). Biotinylated secondary antibody and the Elite Vectastain® kit (Vector Lab, CA, USA) were used for signal detection, while DAB was used as a chromogen substrate. Primary antibodies used were insulin (1:200, Dako, Calif., USA), amylase (1:800, Sigma, Chicago, Ill., USA), and cytokeratin-19 (CK-19) (Phenopath Laboratories, WA, USA).

Activation of point-mutant p53 expression and concomitant heterozygous deletion of Smad4/Dpc4 in the absence of oncogenic Kras$^{G12D}$ (i.e., PD mice) did not affect normal pancreatic development or function. PD animals developed and aged normally, while parenchymal architecture, as well as the synthetic functions of the exocrine and endocrine compartments of the gland, were unperturbed by the genetic manipulations (FIG. 2).

Example 2

Effect of Trp53 Mutant with Dpc4 Deletion on PanIN-to-PDA Progression

The effect of concomitant p53 and Dpc4 mutation on pancreatic neoplasias initiated by oncogenic Kras was investigated to determine whether the histological progression reverted back from the cystic MCN-to-PDA route to the classical PanIN-to-PDA route.

KPD quadruple mutant animals were aged until moribund, and the resulting cancers subjected to comprehensive analyses of gross pathology, histopathology, cellular behaviors and molecular properties. The significance of the data was determined by the Student's t-test (two-tailed) for all in vitro studies. A value of p<0.05 was deemed significant. Fisher's exact t-test was performed for comparison of metastatic disease burdens in KP vs. KPD cohorts. All statistical analyses were done using GraphPad Prizm 5.0 software.

Belying its role as a tumor suppressor gene (TSG), concomitant heterozygous mutation of Dpc4 did not hasten demise when compared with KP mice; both KPD and KP mice had a median survival of approximately 5 months (FIG. 1B). Also, in contradistinction to the macroscopic cystic lesions of the pancreatic body and tail that predominate in KD and KDD animals (Izeradjene et al., 2007), KPD animals develop solid, multinodular tumors of the gland similar to those that develop in KP mice (see FIGS. 3A and 3B). Unexpectedly, the primary tumors in KPD animals were larger, in both size and mass, and occupied more of the organ than KP PDAs (FIGS. 3C and 3D).

The histologic progression in the ducts followed the classical PanIN-to-PDA sequence and not the cystic MCN-to-PDA route. Early grade PanIN lesions were seen in young animals (FIGS. 3E-3G), which subsequently progressed to higher grade PanINs (FIG. 3H) and then to invasive PDA (FIGS. 3I and 3J). Strong expression of CK-19 (FIG. 3F), a epithelial cell marker, confirmed the ductal epithelial nature of these neoplasms, and alcian blue staining revealed abundant cytoplasmic mucin (FIG. 3G). The histologic morphology was predominantly glandular (see FIG. 3I and Table 1), although other less common histologies also seen in human PDAs, including anaplastic and sarcomatoid, could also be found and were similarly rare in the murine tumors (FIG. 3J).

Overall, concomitant mutation of p53 prevents heterozygous deleted Dpc4 from shifting the differentiation state of PanIN lesions initiated by oncogenic Kras toward an MCN phenotype.

KPD animals revealed a further dramatic and unexpected finding—an almost complete absence of metastatic disease. KP animals, by comparison, develop highly metastatic disease to organ sites and with frequencies that faithfully mimic the patterns seen in the majority of patients. Indeed, the heavy macroscopic tumor burden in KP mice, principally to the liver and lungs, contributes significantly to their demise. Liver metastases occur in 63% of KP animals and lung metastases in 44%; overall, fully 74% of KP animals develop metastatic disease (Hingorani et al., 2005). In stark contrast, only 3 of 37 (8.1%) KPD animals developed macroscopically evident metastases and an additional 5 (13.5%) had microscopic metastases only (Table 1; p=0.0001 for the difference between the two genotypes). In the few cases of disseminated disease in KPD animals, metastases were seen only in the liver and never in more distant organs (Table 1), and they did not contribute substantively to overall disease burden.

TABLE 1

Clinical Spectrum of Disease in KPD Mice

| | | | Histology | | Metastases | | | |
|---|---|---|---|---|---|---|---|---|
| ID | Age | PDA | 1° | 2° | Liver | Lung | Ascites | Cachexia |
| 1 | 151 | Y | G | | N | N | Y | * |
| 2 | 169 | Y | G | | N | N | Y | Y |
| 3 | 165 | Y | G | | N | N | N | Y |
| 4 | 329 | Y | G | U | $Y^M$ | N | N | N |
| 5 | 120 | Y | G | U | N | N | * | * |
| 6 | 125 | Y | G | | N | N | Y | Y |
| 7 | 183 | * | * | * | * | * | * | * |
| 8 | 74 | * | * | * | * | * | * | * |
| 9 | 172 | Y | G | U | $Y^M$ | N | N | Y |
| 10 | 193 | Y | G | $C^m$ | N | N | Y | Y |
| 11 | 109 | Y | G | | N | N | N | N |
| 12 | 180 | Y | G | U | $Y^m$ | N | Y | Y |
| 13 | 95 | Y | G | U | $Y^m$ | N | N | Y |
| 14 | 76 | Y | G | | N | N | Y | N |
| 15 | 66 | Y | G | | N | N | N | Y |
| 16 | 102 | Y | N | | N | N | N | N |
| 17 | 190 | Y | G | | $Y^m$ | N | Y | N |
| 18 | 211 | Y | G | U | N | N | N | N |
| 19 | 141 | * | * | * | * | * | * | * |
| 20 | 98 | Y | G | | N | N | N | Y |
| 21 | 73 | Y | G | $C^m$ | $Y^m$ | N | N | Y |
| 22 | 60 | Y | G | | N | N | N | Y |
| 23 | 77 | * | * | * | * | * | * | * |
| 24 | 88 | Y | U | | N | N | N | N |
| 25 | 172 | Y | G | $C^m$; U | $Y^m$ | N | Y | Y |
| 26 | 108 | $Y^1$ | G | | N | N | N | N |
| 27 | 178 | Y | G | | N | N | N | N |
| 28 | 92 | Y | G | U | $Y^M$ | N | Y | N |
| 29 | 78 | Y | G | U | N | N | N | N |
| 30 | 200 | Y | G | | N | N | N | N |
| 31 | 181 | Y | G | | N | N | N | N |
| 32 | 162 | Y | G | | N | N | N | N |
| 33 | 123 | Y | G | | N | N | N | N |
| 34 | 167 | Y | G | | N | N | N | N |
| 35 | 230 | Y | G | | N | N | N | N |
| 36 | 160 | * | * | | * | * | * | * |
| 37 | 165 | * | * | | * | * | * | * |

Y, disease present;
N, no disease detected;
G, glandular;
U, undifferentiated;
$^M$macroscopic;
$^m$microscopic;
* tissue not evaluable secondary to necrosis;
$^1$focally invasive PDA but animal succumbed to thymoma;
C, cystic Thus, the evolution of pancreas cancer in KPD mice is characterized by a shift toward a significantly increased primary tumor burden, together with an almost complete absence of metastatic disease, in contradistinction to the KP mice, but with the overall result of essentially identical survival in these two models of pancreas cancer.

Example 3

Genetic Progression of KPD Pancreas Cancer

To characterize the molecular basis for the very distinct in vivo behavior of KPD PDAs, primary ductal carcinoma cells were purified from the tumors using previously described procedures (Hingorani et al., 2005; Schreiber et al., *Gastroenterology* 127:250, 2004). Pure populations of PDA cells were recovered after 3-4 passages on defined substrates in serum-free culture media. To ensure fidelity to the autochthonous cancers, all subsequent molecular and cellular studies were performed on low passage number cells (less than 15 times for all assays) grown in DMEM/F12 supplemented with 10% FBS, 0.5% Glucose, and 1×Pen/Strep.

To examine recombination events, high-quality total RNA was extracted from cells (about 80% confluency) using TRIzol reagent (Invitrogen, CA, USA), treated with DNase (Applied Biosystems, CA, USA), and further purified using the RNeasy kit (Qiagen, Germany). RNA was quantified using the NanoDrop. For cDNA synthesis, 2 μg total RNA was reverse transcribed using $RT^2$ first strand kit (SA Biosciences).

The isolated PDA cells were examined for recombination and activation of the conditional $Kras^{LSL-G12D}$ and $Trp53^{LSL-R172H}$ alleles, as well as deletion of the Dpc4 allele (FIGS. 3K-3M). Recombination of $Trp53^{LSL-R172H}$ was invariably accompanied by spontaneous loss of the wild-type allele (LOH) (FIG. 3L), as typically occurs in human PDAs with point mutations in one TP53 allele (Hingorani et al., 2005). Interestingly, invasive KPD PDA cells did not undergo LOH at the Dpc4 locus and instead retained the remaining wild-type allele.

For immunoblot analysis, whole cell lysates were prepared using 1×RIPA buffer (Millipore, CA, USA) supplemented with 1×protease inhibitor (Sigma, MO, USA) and phosphotase inhibitor cocktails I and II (Sigma, MO, USA). For immunoblot experiments, 20 μg (murine) or 30 μg (human) whole cell protein lysate were separated on a 4-12% Bis-tris gel system (Invitrogen, CA, USA) and transferred to PVDF membrane (Millipore, CA, USA). Primary antibodies used were Dpc4, p16, p19, Actin (all at 1:2000, Santa Cruz, Calif., USA), and p53 (1:1000, Vector Lab, CA, USA).

These immunoblot analyses confirmed detectable levels of Trp53 consistent with expression of the point-mutant allele as well as persistent, albeit decreased, expression of Dpc4 (as compared with cells with both Dpc4 alleles intact) (FIG. 3N). Interestingly, Cdkn2a/Ink4a (p16) expression was frequently lost, while expression of the contiguous p19 allele was retained, indicating specific promoter methylation rather than genomic deletion as the mechanism for silencing p16. The loss of p16 is notable as prior studies of both KP (Hingorani et al., 2005) and $Kras^{LSL-G12D/+}$:p16/p19$^{-/-}$::Cre (Bardeesy et al., Proc. Natl. Acad. Sci. U.S.A. 103, 5947, 2006) animals found no additional loss of other major TSG during the course of disease progression, identifying non-overlapping mutational spectra in those two model systems. The increased selection pressure to lose p16 in the setting of heterozygous Dpc4 mutation further underscores the latter's behavior as a tumor "promoter" in this particular context.

The spontaneous progression of PDAs with $Kras^{G12D}$, $Trp53^{R172H}$, $Dpc4^{+/-}$ and loss of p16 also represents the first autochthonous model of pancreas cancer encompassing all four cardinal mutations seen in human PDA.

Example 4

Proliferation and Cell Cycle Control in Pancreas Tumor Cells of KPD Mice

The increased primary tumor size at the expense of metastatic disease seen in KPD compared with KP PDAs could potentially be due to increased proliferation, decreased apoptosis, or a combination of both. These different properties were examined in both in vivo resected tumors and in vitro purified primary ductal carcinoma cells.

For immunocytochemistry, the primary antibody used was Ki-67 (1:25, Dako, Calif., USA), which is a marker of proliferating cells. For cell proliferation assays, equal numbers of murine or human cells (30,000) were plated in triplicate for each cell line and incubated in the presence or absence of TGFβ (5 ng/ml, R&D Systems, USA). Cells were counted manually at 24 hour intervals. Data points represent the mean±SEM of triplicate determinations from at least 3 independent experiments. All experiments were conducted in triplicate at least 3 independent times on at least 2 different cell lines from each genetic background. Representative photographs were taken from a minimum of 6-8 separate high power fields. For all assays, media was replaced every 24 hours with or without TGFβ and photographed every 24 hours.

Figure 4:
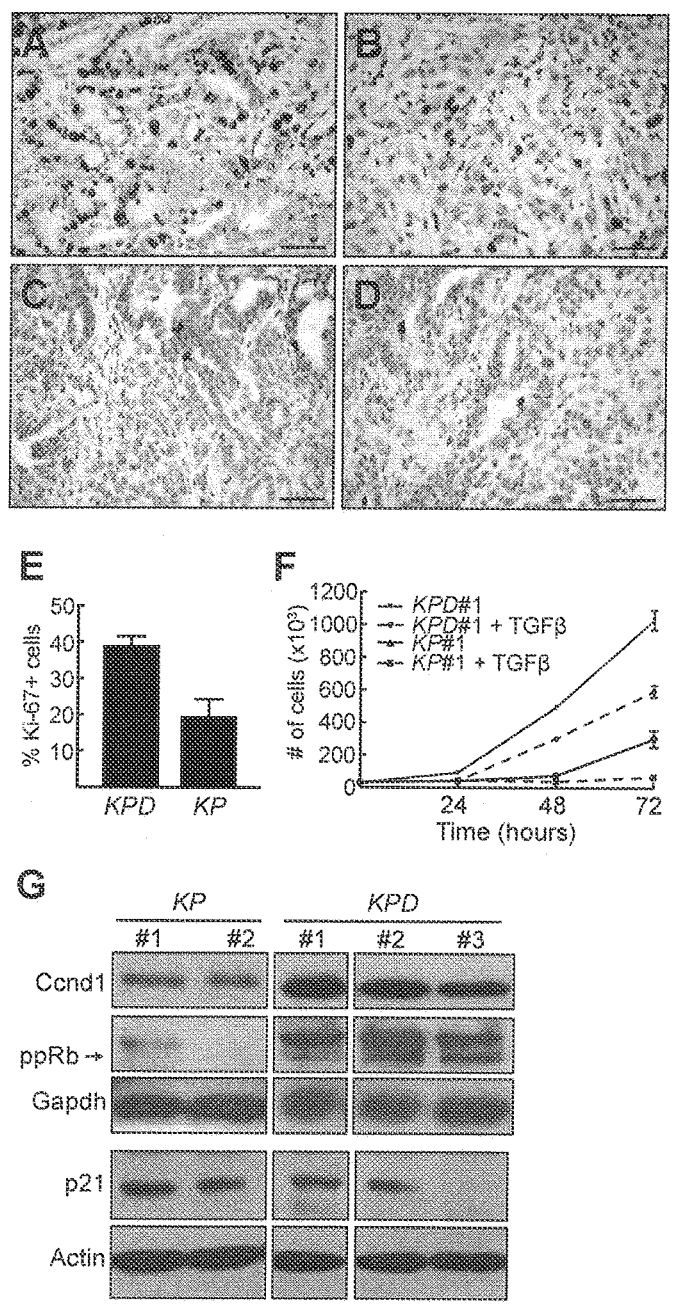

Ki-67 expression was significantly increased in KPD versus KP tumors (40% vs. 20%, p=0.0114; FIGS. 4A, 4B and 4E). Apoptosis, however, was similarly negligible in PDAs in both genetic contexts (FIGS. 4C and 4D). Primary KPD PDA cells in culture also had a higher proliferative rate than KP cells (FIG. 4F), and once again very similar and low apoptotic rates (not shown). KPD cells were only partially growth-arrested by TGFβ (FIG. 4F).

Immunoblots were used to characterize the expression of several additional critical cell cycle components and the primary antibodies used were CyclinD1, Actin, and GAPDH (all at 1:2000, Santa Cruz, Calif., USA); p53 (1:1000, Vector Lab, CA, USA), ppRb$^{780}$ (1:1000, Cell Signaling, MA, USA); and p21 (1:1000, AbCam, MA, USA). These data show that the higher proliferative index of KPD cells could be attributed to higher basal levels of cyclins D1 (FIG. 4G) and E1 (data not shown), which bind to and activate Cdk4 and Cdk2, respectively; lower levels of p21 (FIG. 4G); and correspondingly increased levels of phosphorylated Rb (FIG. 4G), liberating E2F to promote cell cycle entry.

Overall, these data indicate that increased primary tumor size seen in KPD compared with KP PDAs appears to be due to increased proliferation with no alteration in apoptosis levels.

Example 5

Effect of Dpc4 Mutation on EMT and Migration of KPD Cells In Vitro

A series of functional assays were performed to further explore the almost complete absence of metastatic disease in KPD pancreas cancers. For all experiments, a single retained wild-type Dpc4 allele and correspondingly reduced protein expression (i.e., about 50% of WT levels) were confirmed in KPD cells prior to assay (FIG. 3N and data not shown). The in vitro assays, while reflective of only some of the capabilities necessary for in vivo metastasis, nevertheless underscore the profoundly distinct intracellular wiring and responses to external stimuli in KP and KPD cells.

First, KPD pancreas cancer cells were probed by immunofluorescence for their ability to undergo epithelial-to-mesenchymal transition (EMT), a program of morphological and molecular changes implicated in the metastatic phenotype. Briefly, cells were grown on glass cover slips and treated for 72 hours in the presence or absence of TGFβ (5 ng/ml); media was replaced every 24 hours. For E-cadherin immunofluorescence, cells were fixed in ice cold methanol: acetone (1:1) for 15 minutes. For F-actin IF, cells were fixed in 4% paraformaldehyde for 30 minutes at RT followed by brief rinse in 0.15M glycine to quench the PFA. After fixation, the cells were washed with PBS and blocked for 1 hour at RT with 2% fatty acid-free BSA/2.5% goat serum. Cells were incubated with E-cadherin primary antibody (1:200, BD Biosciences) or Alexafluor488 F-actin (1:1000) for 1 hour at RT. Alexafluor 488 secondary antibody was used to visualize E-cadherin antibody. Cells were counterstained with DAPI and the slips mounted with Prolong Gold Anti-fade (Invitrogen, CA, USA). Images were acquired using a Nikon Eclipse 80i microscope with NIS Elements Software (Nikon, v3.1).

Figure 5:
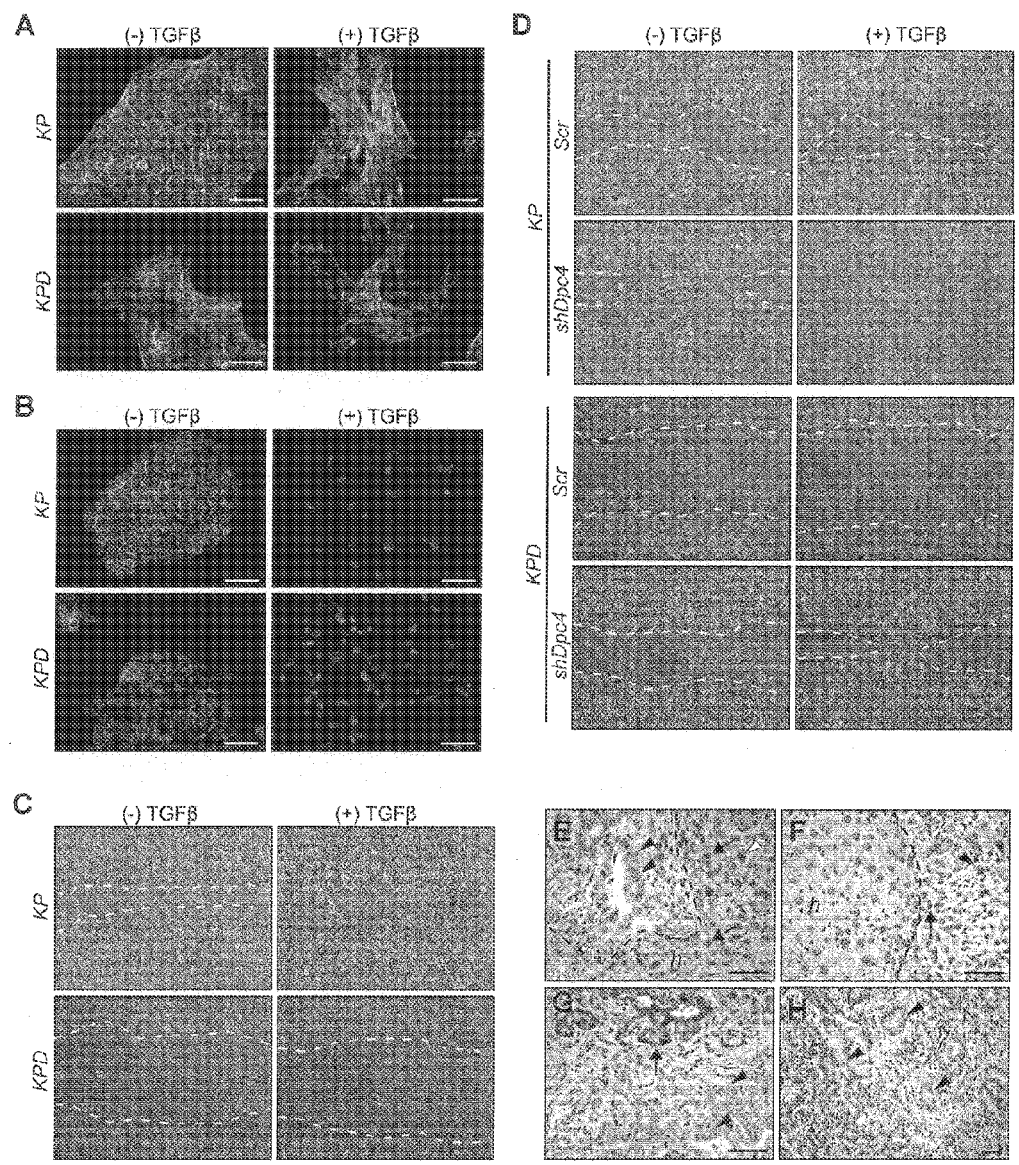
Figure 6:
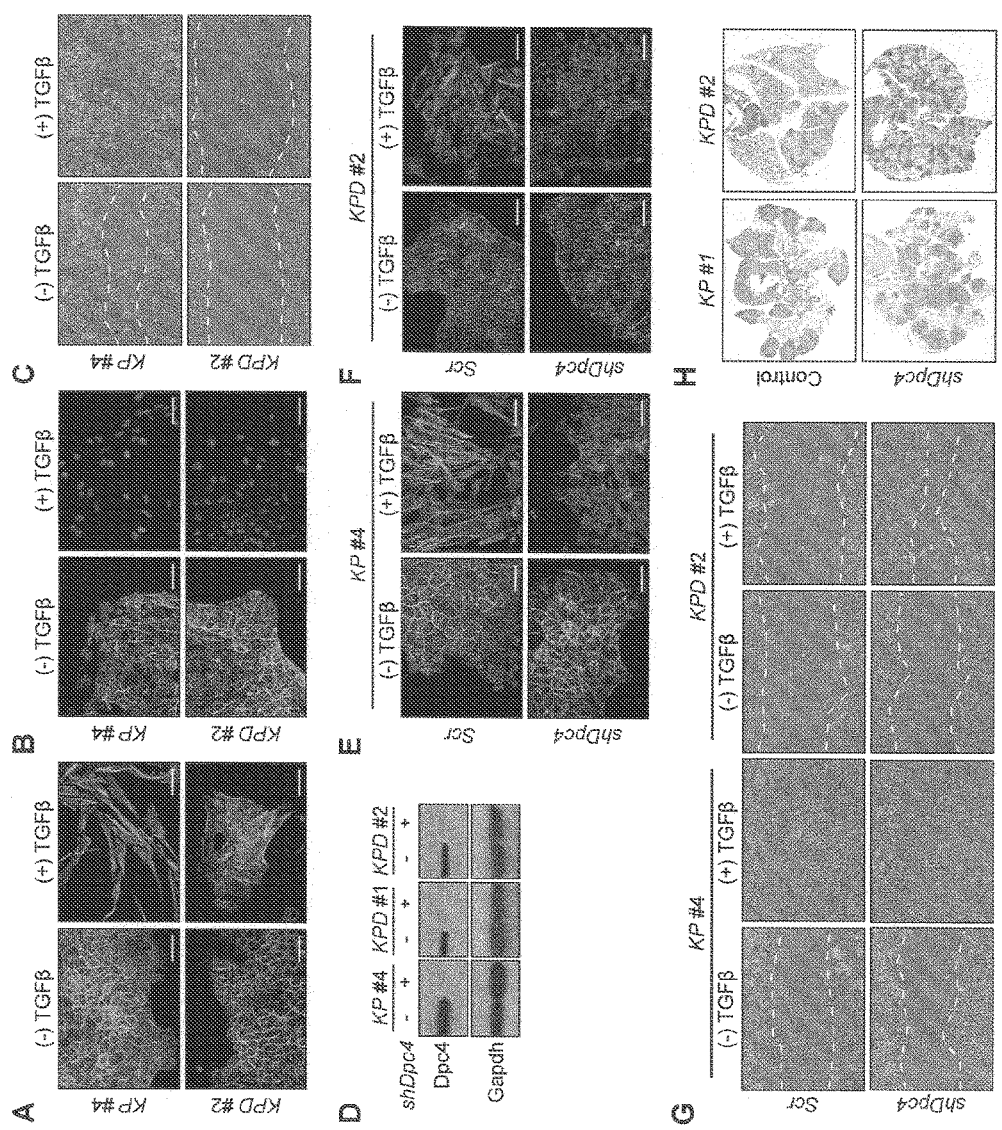

KPD carcinoma cells did develop, if perhaps less abundantly, actin stress fibers in response to TGFβ (FIGS. 5A and 6A), while also down-regulating surface expression of E-cadherin, a member of the superfamily of $Ca^{2+}$-dependent adhesion proteins that, in part, defines the epithelial phenotype (FIGS. 5B and 6B). Also, KP PDA cells readily underwent TGFβ-induced EMT (FIGS. 5A, 5B, 6A and 6B). Hence, these data show that EMT is essentially intact in KPD PDA cells.

In addition to examining EMT, carcinoma cells were examined for their ability to migrate. For migration assays, cells were first incubated in the presence or absence of TGFβ (5 ng/ml) for 60 hours to achieve growth arrest (in order to separate out effects of proliferation rather than migration; see Izeradjene et al., 2007), then serum starved for 8 hours. Confluent cultures were scratched with a 20 μl pipette tip to generate a wound in three horizontal stripes per well; each experimental condition was performed in triplicate wells. All experiments were conducted in triplicate at least 3 independent times on at least 2 different cell lines from each genetic background. A minimum of six points across each wound were assessed independently by two investigators at the indicated time intervals for the presence of cells within the expanse. Representative photographs were taken from a minimum of 6-8 separate high power fields. For all assays, media was replaced every 24 hours with or without TGFβ and photographed every 24 hours.

Despite the qualitative ability to undergo EMT, the basal migration of KPD cells across an introduced wound in monolayer culture was significantly decreased compared with KP cells; moreover, the migration of KP cells was stimulated by TGFβ, while KPD cells did not respond in kind (FIGS. 5C and 6C).

Again, both the baseline properties as well as the response to TGFβ were very different in the presence or absence of heterozygous Dpc4 mutation.

Example 6

Effect of Dpc4 Mutation on EMT and Migration of KPD Cells In Vivo

Purified KP and KPD carcinoma cells were also injected into the circulation of immunocompromised mice and scored for their ability to form pulmonary metastases. Briefly, murine cells were studied in a classical tail vein metastasis assay in nude mice (Athymic NCr-nu/nu). At least 3 animals were injected ($1\times10^5$ or $1\times10^6$ cells/injection, depending on the experiment) for each independently derived cell line and all experiments were performed at least twice. Animal health was monitored daily and all study animals in a given cohort were sacrificed when any of the animals in that particular group showed signs of cachexia, lethargy, or distress. Metastatic disease burdens were assessed as a ratio of cross-sectional area occupied by tumor to whole lung area using ImageJ software (NIH).

KP cells formed numerous, large, pleural and parenchymal metastases leading to demise from respiratory failure. KPD cells, on the other hand, formed far fewer and smaller metastatic deposits in the lungs of animals that appeared clinically robust at comparable time points (FIG. 6H, top panels). These results parallel what was observed in the in vitro immunofluorescence assay of Example 5.

Example 7

Effect of Late Dpc4 Mutation on Metastatic Capability of Invasive KP Carcinoma Cells These experiments examine whether late mutation of Dpc4 (i.e., after the acquisition of an already invasive phenotype) would not inhibit the ability of PDA cells to metastasize by assessing the functional consequences of knockdown of Dpc4 expression in KP invasive carcinoma cells (FIG. 6D).

Dpc4 expression was knocked down using a short hairpin RNA (shRNA) sequence (GAUUAACACUGCAGA-GUAA, SEQ ID NO.: 19) targeting murine DPC4 procured in a pGIPZ vector (Open Biosystems). A control sequence (scrambled, scr) was used as a negative control. High-titer lentivirus was made and PDA cells were infected and selected for stable expression of the DPC4-specific shRNA. Knockdown was confirmed by qRT-PCR. Briefly, total RNA was reverse transcribed using the high capacity cDNA synthesis kit (Applied Biosystems, CA, USA) and qRT-PCR performed using SYBER green supermix (Bio-Rad, VA, USA) on a CFX-96 thermal cycler. PCR reactions included initial denaturation at 95° C. for 5 minutes, followed by 40 cycles of incubation at 95° C. for 30 seconds and 60° C. for 1 minute. Melting curves were generated for each reaction to exclude false positive signal from primer dimers. Murine CphA was used as an internal control (forward primer SEQ ID NO.:11, GAGCTGTTTGCAGACAAAGTTC; and reverse primer SEQ ID NO.:12, CCCTGGCACATGAATC-CTGG). DPC4 transcript levels in murine cell lines were analyzed by qRT-PCR using the Taq-man assay per the manufacturer's recommendations (Applied Biosystems, CA, USA) with GAPHD as an internal control.

Tellingly, late ablation of Dpc4 expression in KP PDA cells did not completely prevent EMT in response to TGFβ. Some of the morphological changes associated with EMT (e.g., actin stress fiber formation) were still evident (FIG. 6E), although the cells did exhibit less of a tendency to separate from each other. Even after complete loss of Dpc4 expression in KPD carcinoma cells some morphological features of EMT in response to TGFβ also persisted (FIG. 6F). More startlingly, not only did depletion of Dpc4 in KP cells not decrease their migration, but instead migration increased slightly, and TGFβ still promoted this motility (FIGS. 5D and 6G). Complete ablation of Dpc4 expression in KPD cells also increased their basal migratory behavior modestly, which was again further potentiated by TGFβ (FIGS. 5D and 6G), perhaps awakening a previously dormant metastatic phenotype.

Finally, results from in vivo pulmonary metastasis assays were consistent with the in vitro migration data, revealing that complete knockdown of Dpc4 in KPD cells enhanced their metastatic potential, and completely extinguishing Dpc4 in KP cells did not diminish their already considerable metastatic potential (FIG. 6H).

In view of the results of these in vitro migration and in vivo metastasis assays, the status of Dpc4/Smad4 in paired primary and metastatic tumors in the very few KPD animals that had developed metastases was analyzed. Liver metastases of KPD animals showed loss of nuclear Dpc4 expression (FIGS. 5E and 5F), and examination of the respective primary tumors revealed focal loss of Dpc4 (FIGS. 5G and 5H), indicating a potential source for the disseminated cells.

Thus, late loss of Dpc4 in invasive KP carcinoma cells further unleashes its invasive and metastatic behavior, while completing the loss of Dpc4 in cells that underwent heterozygous Dpc4 deletion prior to the development of an invasive phenotype (i.e., as in KPD cells) bestows a newly acquired metastatic potential.

Example 8

Role of Runx3 in Pancreas Cancer Metastasis

To further examine the dramatically different behaviors of KP and KPD carcinomas in otherwise nearly identical genetic contexts, comparative profiling was performed. Initially, the profiling was focused on the TGFβ-Smad signaling pathway genes. Expression array analyses on purified KP and KPD primary carcinoma cells (n=3 each) using a customized TGFβ-signaling specific quantitative real time—PCR platform was performed. Array analyses with SYBR Green PCR Master Mix (SA Biosciences) were carried out according to the manufacturer's protocol on a Bio-Rad CFX-96 PCR System (Bio-Rad, VA, USA). Gene expression differences were determined using the $2^{-\Delta\Delta Ct}$ method following standard protocols (SA Biosciences). Human CPHA was used as an internal control

```
(forward primer,
                                    SEQ ID NO.: 13
CCCACCGTGTTCTTCGACATT;
and reverse primer,
                                    SEQ ID NO.: 14
GGACCCGTATGCTTTAGGATGA).
```

There were 15 genes identified as being up-regulated at least 2-fold in KP cells as compared to KPD cells, which might represent metastasis-promoting genes (Table 2). As expected, Smad4 expression was approximately 2-fold higher in KP than KPD cells. Completely distinguishing itself, however, was Runx3, which was up-regulated 36-fold in KP cells (Table 2 and FIG. 7A).

TABLE 2

TGFβ Pathway Array
Analysis of KP vs. KPD PDA
Cells*

| Gene | Fold Change |
| --- | --- |
| Runx3 | 36.0541 |
| Dlx2 | 7.4322 |
| Tgfbi | 4.6685 |
| Id1 | 3.1935 |
| Itgb5 | 3.1581 |
| Ltbp2 | 3.1563 |
| Ltbp1 | 3.0789 |
| Bmper | 2.997 |
| Tgfb1i1 | 2.9623 |
| Itgb7 | 2.6516 |
| Bmp1 | 2.4641 |
| Smad4 | 2.3829 |
| Tgfb3 | 2.3613 |
| Smad5 | 2.1156 |
| Bmpr1a | 2.0592 |

*Genes upregulated at least 2-fold in KP compared to KPD carcinoma cells. Values are expressed as fold change (n = 3 each).

To further define the role of murine Runx3 in the biological behavior of PDA, qRT-PCR (forward primer SEQ ID NO.:17, AGAGTTTCACGCTCACAATC; and reverse primer SEQ ID NO.:18, GGAGAAGGGGTTCAGGTC) was used established that transcript levels correlated with metastatic potential in a larger series of primary cell lines. KP PDA cells had approximately 20-fold higher Runx3 expression than KPD cells by quantitative PCR (200-fold and 10-fold respectively, relative to WT ductal cells; n=3 each, FIG. 8A). Transcript levels corresponded to protein levels (FIG. 8B).

As a transcription factor, the subcellular localization of Runx3 is also of functional consequence, so isolated cytoplasmic and nuclear fractions from KP and KPD cells were examined. Nuclear and cytoplasmic fractions of murine PDA cell lines were prepared using the nuclear cytoplasmic kit from Active Motif (CA, USA). Approximately 20 μg of nuclear and cytoplasmic cell fractions were loaded on 4-12% Bis-Tris gel and probed with mouse Runx3 (1:500, GenScript, NJ, USA). Also used were Parp (1:1000) and Gapdh (1:2000, both from Santa Cruz Biotechnology, CA, USA, which were used as nuclear and cytoplasmic markers, respectively.

The data show that both types of carcinoma cells express Runx3 in the nuclear compartment (FIG. 7B), albeit at different levels, consistent with the qRT-PCR and immunoblot data. Specific immunohistochemistry for Runx3 revealed no discernible expression in normal ducts and acini, while islets showed predominately cytoplasmic Runx3 staining (FIG. 8C). KP tumors (FIGS. 8D-8F) had moderate to strong nuclear Runx3 staining, whereas KPD tumors (FIGS. 8G and 8H) showed very weak expression at best. Preinvasive lesions adjacent to KP carcinomas were also negative for Runx3 expression (FIG. 8D). Both KP and KPD tumors showed strong nuclear staining in infiltrating lymphocytes, a common site for elevated Runx3 and a useful internal control (Yarmus et al., *Proc. Natl. Acad. Sci. U.S.A.* 103:7384, 2006).

Figure 7A:
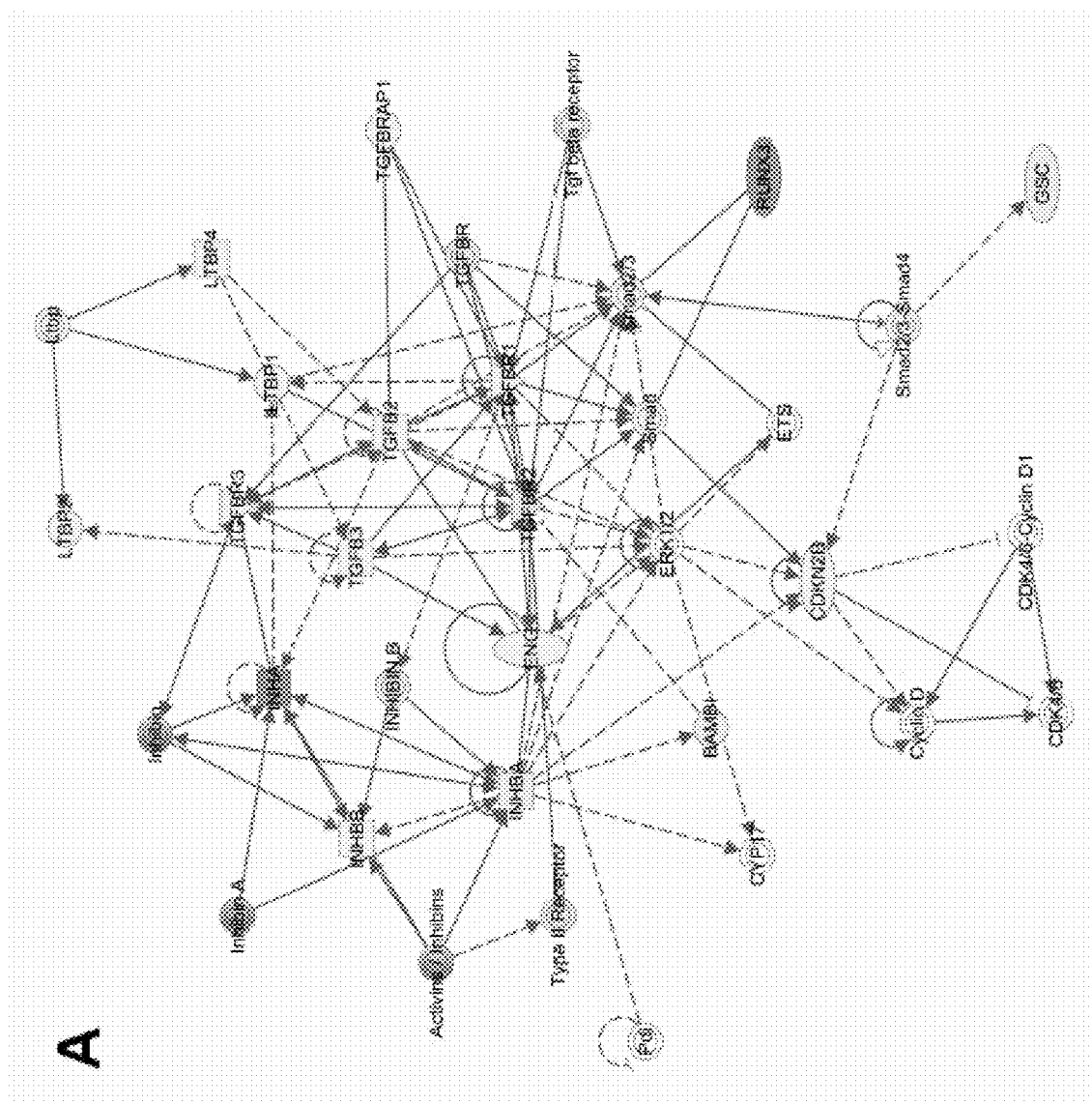
Figures 7B, 7C, 7D, 7E, 7F, 7G, 7H:
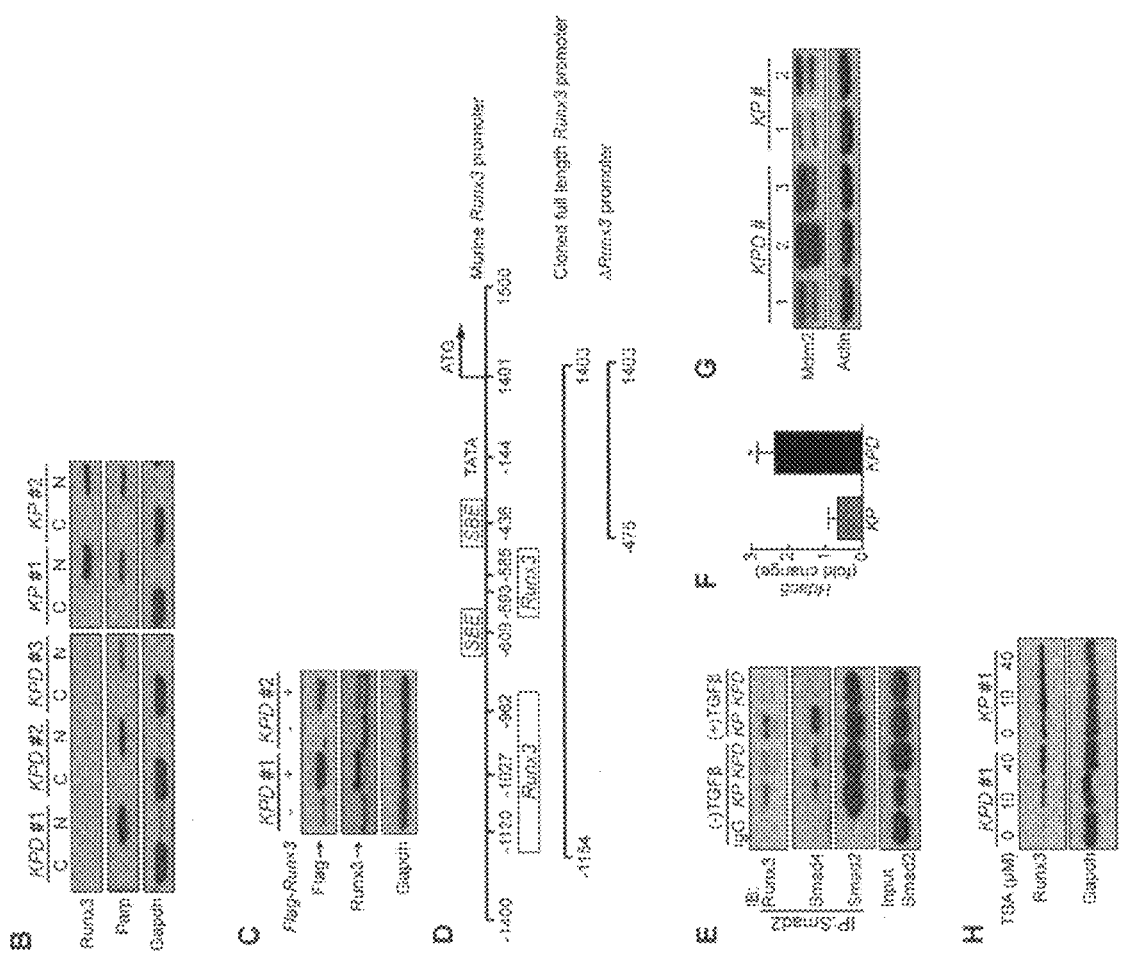

To further investigate its effects on metastatic potential, Runx3 was stably over-expressed in two different primary KPD carcinoma cell lines (FIG. 7C). Briefly, full length mouse Runx3 was obtained from Open Biosystems (Huntsville, Ala., USA) and subcloned into a pMSCV Puro IRES GFP vector (Addgene, MA, USA) to generate a Flag-Runx3 construct. Fidelity of the cloned genes was confirmed by sequencing. High-titer retrovirus was made in HEK293T cells using a standard protocol (Addgene, MA, USA). Cells were selected with the appropriate antibiotic for at least 5 days or until all uninfected cells were dead. Transgene expression was confirmed by immunoblot using Flag tag-specific and Runx3-specific antibodies.

Runx3 overexpression greatly increased the basal migration of KPD cells (FIG. 8I), which was also less sensitive to attenuation by TGFβ, behaviors more reminiscent of KP cells than basal KPD cells. KPD-Runx3 cells also formed significantly increased numbers of pulmonary metastases in immunocompromised mice, a property virtually absent from control transfected KPD cells and again more like KP cells (FIGS. 8J and 8K).

Example 9

Regulation of Runx3 Levels

The following experiments were performed to investigate the potential mechanisms that regulate basal levels of Runx3. Analysis of the promoter region of the murine Runx3 locus revealed five consensus-binding sites for Runx3 itself clustered into two groups (FIG. 7D). An electrophoretic mobility shift assay (EMSA) was performed using nuclear and cytoplasmic protein fractions extracted according to manufacturer's protocol (Active Motif, CA, USA) and protein concentrations determined by Bradford assay (Bio-Rad, VA, USA). Complimentary oligonucleotide sequences were designed to span two putative consensus Runx3 binding sites—(1) mRunx3EMSAF1: GGTCCCTCAACCACA-GAACCACAAGGCCAGGCCCT (SEQ ID NO.:2) and (2) mRunx3EMSA complement1: CCAGGGAGTTGGT-GTCTTGGTGTTCCGGTCCGGGA (SEQ ID NO.:3). The oligonucleotides were end-labeled with Biotin 3' end-labeling kit (Thermo Scientific, IL, USA). Nuclear protein extracts (10 µg) were incubated with labeled probe+/− 4-fold excess unlabeled probe for 20 minutes at room temperature and separated on 7.5% nondenaturing polyacrylamide gels. Resolved protein-DNA complexes were transferred to nylon membrane and processed for detection using Light Chemiluminescent EMSA kit (Thermo Scientific, IL, USA).

The EMSA showed that nuclear extracts from KP carcinoma cells bound the probes specifically (FIG. 8L). To determine if these Runx3 sites were functionally responsive to Runx3, a full length murine Runx3 promoter (containing 5 putative Runx3 binding sites) and a truncated version lacking Runx3 binding sites were each cloned into a pGL2-luciferase expression vector (Promega, Wis., USA) to perform a luciferase reporter assay. Full length or truncated Runx3 promoter (0.1 µg) constructs were co-transfected with increasing concentrations of Flag-Runx3 along with 0.05 µg of the n-gal plasmid into HEK293T cells. Cell lysates were prepared at 48 hours in Reporter Lysis Buffer (Promega Wis., USA), substrate added and luciferase activity recorded on a luminometer (Veritas, Wis., USA). β-gal activity was used to normalize the transfection efficiency. Results represent means±SEM of triplicate wells from three independent experiments.

The luciferase assay showed that increased levels of Runx3 led to increased expression of the luciferase reporter (FIG. 8M). These data indicate that Runx3 binds to its promoter and increases its own transcription through a positive feedback mechanism.

Example 10

Regulation of Runx3 Levels at the Transcriptional Level

As transducers of TGFβ signaling, the Runx family of transcription factors is known to interact with R-Smads. Interestingly, the Runx3 promoter region also contains two canonical Smad binding elements (FIG. 7D), indicating potential transcriptional control by R-Smads as well. In silico analyses of promoter regions of various genes for putative Runx3 binding sites and SBE (SMAD binding elements) were performed with publically available software (see, e.g., www.cbrc.jp/research/db/TFSEARCH.html) and regions up to −1200 bp upstream of the transcription start site (+1 TSS) were examined.

To examine whether the transcriptional activity of Runx3 was exercised in complex with Smad4/Dpc4, immunoprecipitation assays were performed. Briefly, cells were lysed by sonication in 20 mM HEPES (pH 7.5), 400 mM KCl, 5% Glycerol, 5 mM EDTA, 0.4% Np40, supplemented with 1×protease inhibitor (Sigma, MO, USA), phosphotase inhibitor cocktails I and II (Sigma, MO, USA), and the lysates cleared by centrifugation. Extracts were diluted to 20 mM HEPES (pH 7.8), 50 mM KCl, 5% Glycerol, 2.5 mM MgCl2, 0.05% NP40 and incubated with Smad2 antibody (2.5 µg/ml from AbCam, Cambridge Mass., USA) and Protein A-Sepharose beads for 4 hours at 4° C. Beads were washed and co-purified proteins liberated in boiling Laemmli buffer and analyzed by immunoblot with the appropriate primary antibody. ExactaCruz secondary antibodies (Santa Cruz biotechnology) were used to reduce background from IgG.

The immunoprecipitation data show that Runx3 was co-immunoprecipitated in complexes with Smad2 and Smad4 and, furthermore, more complex formation occurred in KP cells as compared to KPD cells (FIG. 7E). Moreover, TGFβ appeared to favor complex formation in KP cells and inhibit it in KPD cells, echoing its opposing effects on their respective cell behaviors. In addition, exogenous over-expression of Smad4 increased Runx3 levels in KPD cells (FIG. 8N), while targeted depletion of Smad4 (using SEQ ID NO.: 19) had the converse effect (FIG. 8O).

In sum, Runx3 appears to control its own transcription in complexes with Smad4.

Example 11

Regulation of Runx3 Levels at the Post-Translational Level

A positive feedback loop may mean that a certain threshold of activity would be needed for Runx3 transcriptional activation to result in rapid amplification of the system; thus, the resting levels of the Runx3 protein might be subject to multiple levels of control. Indeed, both histone deacetylases (Hdac) and ubiquitin-coupled degradation have been implicated in a concerted mechanism for regulation of the Runx family of proteins—Hdacs remove acetyl groups from critical lysine residues on Runx proteins exposing them to Mdm2-mediated ubiquitination and targeted degradation (Bae and Lee, *Gene* 366:58, 2006; Chi et al., *Cancer Res.* 69:8111, 2009). The class II Hdacs (Hdac-4 and -5), specifically, have been shown in other contexts to be most important for regulating Runx3 (Jin et al., *J. Biol. Chem.* 279:29409, 2004).

Quantitative RT-PCR showed that expression of murine Hdac5 (forward primer SEQ ID NO.:15, AGCCCAC-CACGTTCTTTG; and reverse primer SEQ ID NO. 16, GTCATCACGGCTGTCATAGGG) was approximately 3-fold higher in KPD carcinoma cells (n=3) than KP cells (n=3) (FIG. 7F). In addition, resting levels of Mdm2 protein (detected with primary antibody at 1:2000, Santa Cruz, Calif., USA) were significantly higher in KPD than in KP cells (FIG. 7G).

To directly test of this potential involvement of Hdac5 in the post-translational control mechanism of Runx3, a histone deacetylase inhibitor was used to determine whether Runx3 levels increased when deacetylation of Runx3 by Hdac5 was minimized or abrogated (i.e., whether the acetylation level of Runx3 does in fact affect physiologic degradation). Briefly, cells ($4\times10^5$) were plated in 60 cc dishes and trichostatin A (TSA) (Tocris Biosciences, MO, USA), an Hdac5 inhibitor, was added at 0, 10, or 40 µM at 24 hours. Total RNA or whole cell lysates were prepared as described herein after 48 hours of treatment, and the latter resolved on 4-12% Bis-Tris gels, transferred to PVDF and probed with Runx3 antibody.

Treatment of KPD carcinoma cells with TSA did indeed raise levels of Runx3 to approximately those found in KP cells (FIG. 7H).

Thus, a plausible mechanism for setting Runx3 levels in epithelial cells may involve autologous transcriptional control, as well as post-translational modifications and degradation. The elevated basal levels of Hdac5 and Mdm2 in KPD cells, together with decreased levels of Smad4 available to form activating transcriptional complexes, probably helps maintain Runx3 below a critical set-point, but decreasing the levels or activities of either enzyme (ubiquitin ligase or deacetylase) would probably allow Runx3 levels to rise above this threshold where it could rapidly amplify its effects by increasing its own transcription.

Example 12

Role of Runx3 in Human Pancreas Cancer Cells

Figure 9:
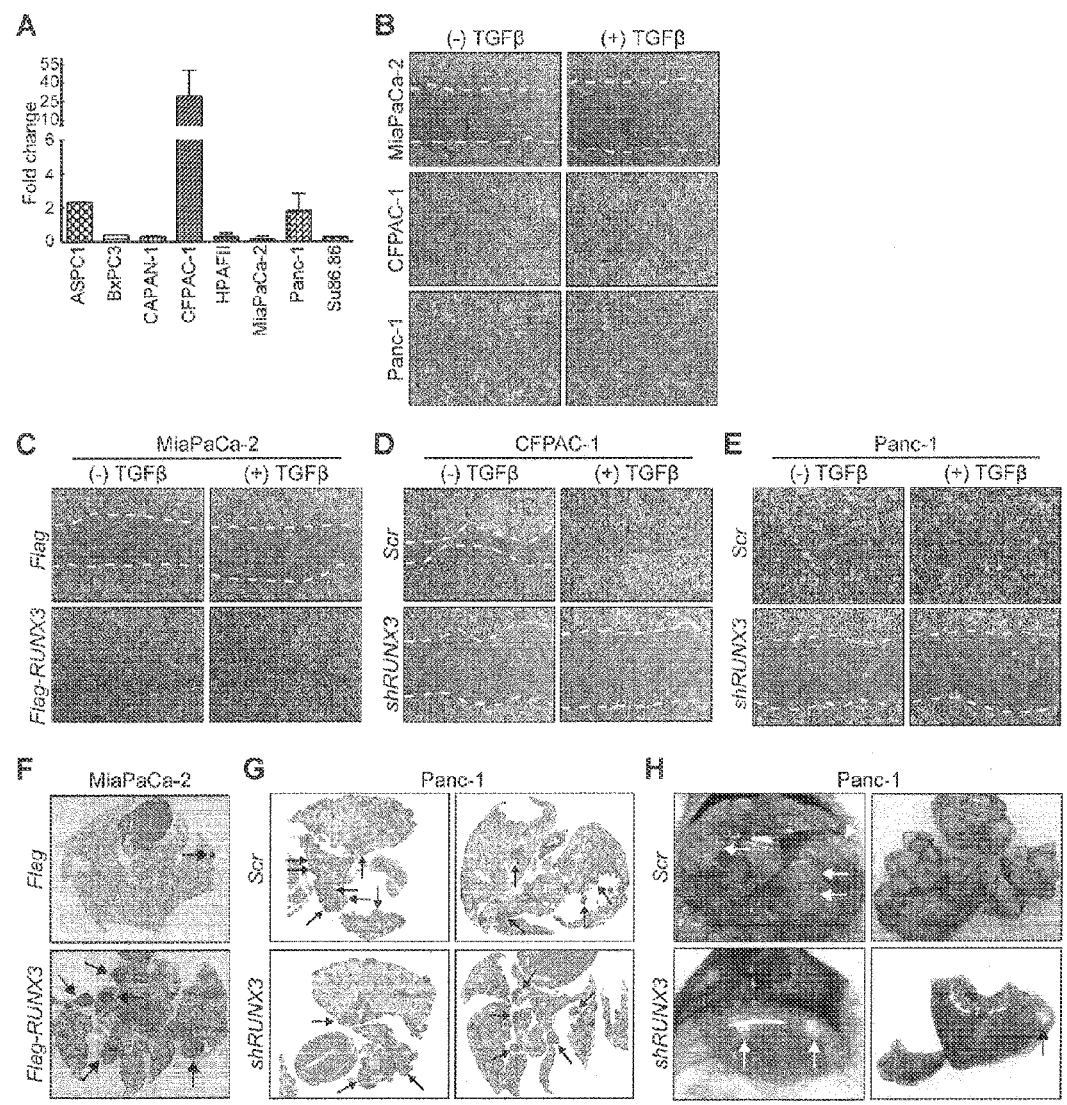

To investigate the role of RUNX3 in human pancreas cancer cells, RUNX3 protein levels were assessed in a panel of well-characterized human pancreatic cancer cell lines, which were compared to non-transformed human pancreatic ductal epithelial (HPDE) cells in a qRT-PCR assay (FIG. 9A). From this series, the lowest (MiaPaCa-2) and two of the highest (CFPAC1 and Panc-1) RUNX3-expressing lines were chosen for further study. The primary antibody used to detect human RUNX3 was R35G4 (1:500, AbCam, MA, USA).

As an initial analysis, the human pancreas cancer cell lines were tested in the scratch wound migration assay described herein. The basal levels of RUNX3 in these human PDA cell lines correlated with their migratory potential, as MiaPaCa-2 cells migrated far less well than CFPAC-1 and Panc-1 cells (FIG. 9B). Moreover, the respective responses of these human cell lines to TGFβ also followed the pattern seen with murine PDA cells. That is, TFGβ modestly inhibited the migration of MiaPaCa-2 cells, as it similarly did for low Runx3-expressing KPD cells, whereas it promoted or left unaffected the high basal migration of CFPAC1 and Panc-1 cells (FIG. 9B), similar to high-Runx3 expressing KP cells.

Human RUNX3 was cloned into pBABE hygromycin vector and stable RUNX3 expressing HEK293T cells were prepared using a similar protocol to that used to make the murine version. Also, shRNA sequences targeting human RUNX3 to knock down expression were procured in pGIPZ vectors (Open Biosystems). High-titer lentivirus was made and PDA cells were infected and selected for stable expression of the RL//VX3-specific shRNA (SEQ ID NO.: 20, CGGCAGAAGCUGGAGGACC). Knockdown was confirmed by qRT-PCR.

Overexpression of human RUNX3 in MiaPaCa-2 cells greatly increased their migration (FIGS. 9C and 10A). Conversely, depletion of RUNX3 in CFPAC1 and Panc-1 cells inhibited their migration (FIGS. 9D, 9E, 10B and 10C).

To determine whether overexpression of RUNX3 in human PDA cells also promotes metastasis, pulmonary metastasis assays were performed using NOD/SCID mice. MiaPaCa-2 cells overexpressing RUNX3 showed a significantly greater metastatic burden compared to cells transfected with control vector (FIG. 9F). Similarly, Panc-1 cells, with and without targeted depletion of RUNX3, were found to have their overall metastatic potential decreased considerably as compared to control cells. Interestingly, both control and RUNX3-knockdown Panc-1 cells produced a comparable number of lung metastases (FIG. 9G); however, the ability of Panc-1 cells to seed and support secondary metastases to the liver was considerably decreased by RUNX3 depletion (FIG. 9H), which was reflected in the overtly distinct gross pathology and significantly different liver weights between the two groups: 4.3 +/−0.6 g (n=4) vs. 0.53+/−0.06 g (n=3), for control and knockdown cells, respectively.

Thus, the RUNX3-dependent metastatic drive and responses to TFGβ observed in human PDA cells parallels the phenotypes and behaviors seen in the murine counterpart PDA cells.

Example 13

Role of Runx3 in Establishment of a Metastatic Niche

The inability of KPD cells to efficiently seed metastases even after direct introduction into the bloodstream indicated that they may differ from KP cells in more than just the ability to migrate. Of interest was how the tumor epithelium refashions its microenvironment, including the nascent metastatic niche, not only to resist systemic therapy (Provenzano et al., Cancer Cell 21:418, 2012) but to also support growth, invasion, and disease dissemination. Accordingly, focused array profiling for ECM genes comparing the highly metastatic KP and non-metastatic KPD carcinoma cells was performed.

A survey of the top differentially expressed genes revealed a number of genes previously associated with critical ECM functions involved in local invasiveness and modeling of the metastatic niche (Table 3), including matrix metalloproteinases such as MMP2, 10 and 11 (Krantz et al., Mol. Cancer Res. 9:1294, 2011); Timps (Schelter et al., Clin. Exp. Metastasis 28:793, 2011); Versican (Kim et al., Nature 457:102, 2009; Said et al., J. Clin. Invest. 122:1503, 2012); Spp1 (Ding et al., Nature 470:269, 2011; Dudley et al., Cancer Cell 14:201, 2008); and Sparc (Bradshaw, J. Cell. Commun. Signal. 3:239, 2009).

TABLE 3

| ECM Focused PCR Array in KP vs. KPD PDA Cells* | |
|---|---|
| Gene | Fold Change |
| Col6a1 | 12.5194 |
| Sparc | 8.3402 |
| Vcan | 7.6945 |
| Spp1 | 7.1535 |
| Timp3 | 6.9182 |
| Mmp10 | 6.4396 |
| Cdh2 | 4.3222 |
| Tgfbi | 4.2408 |
| Fbln1 | 3.557 |
| Thbs1 | 3.3539 |
| Mmp2 | 3.1125 |
| Adamts1 | 3.0894 |
| Ecm1 | 2.9625 |
| Vcam1 | 2.8629 |
| Fn1 | 2.7477 |
| Sgce | 2.7383 |
| Mmp11 | 2.7008 |
| Thbs3 | 2.5626 |
| Ncam1 | 2.4502 |
| Col5a1 | 2.0393 |

TABLE 3-continued

ECM Focused PCR Array in KP vs. KPD PDA Cells*

| Gene | Fold Change |
| --- | --- |
| Timp2 | 2.0159 |
| Selp | 2.013 |
| Ctgf | 1.9957 |

*Genes upregulated at least 2-fold in KP compared to KPD carcinoma cells. Values are expressed as fold change (n = 3 each).

One of the most highly upregulated genes in KP compared to KPD carcinoma cells was osteopontin (SPP1), which was previously found to be upregulated in human PDA and shown to increase the invasion of human PDA cell lines in vitro (Kolb et al., *Cancer Biol. Therap.* 4:740, 2005). But, some genes showing upregulation, including the top-ranked one, Col6a1, were less familiar (Table 3 and FIG. 11A).

With regard to COL6A1 gene, little is known about its specific function(s) in cancer and, in particular, the pathogenesis of PDA. But, COL6A1 has been shown to associate in specific and structural binding interactions with HA (Kielty et al., *J. Cell Biol.* 118:979, 1992; McDevitt et al., *FEBS Letters* 294:167, 1991) and also to bind to fibrillary type I collagen (Bonaldo et al., *Biochemistry* 29:1245, 1999), which is itself complicit in the aggressiveness and metastatic dissemination of PDA (Armstrong et al., *Clin. Cancer Res.* 10:7427, 204; Shields et al., *Biochem. J.* 441:541, 2012; Shintani et al., *Cancer Res.* 66:11745, 2006). In addition, COL6A1 has been identified in the serum proteome of PDA patients (Pan et al., *PLoS One* 6:e27574, 2011; Yu et al., *J. Proteome Res.* 8:1565, 2009).

Another interesting finding was that CD44, the surface receptor for hyaluronic acid (HA), was also upregulated in KP cells as compared to KPD cells, albeit to a slightly lesser extent (1.7-fold, data not shown). Thus, an additional benefit of degrading HA in PDA may derive from disrupting this well-known signaling pathway (Toole, *Nat. Rev. Cancer* 4:528, 2004). Thus, in certain embodiments, PDA may be treated with a RUNX3 inhibitor in combination with degrading HA, disrupting the CD44 signaling pathway (Toole, *Nat. Rev. Cancer* 4:528, 2004), or a combination thereof.

Example 14

Role of SPP1 and COL6A1 in Pancreas Cancer Cell Behavior

To examine the potential role of SPP1 and COL6A1 in metastatic niche formation in PDA, the promoter regions and expression patterns of these genes, as well as their effect on cell behavior, were analyzed.

Immunoblots were performed as described herein, wherein the primary antibodies used were Actin (control) (1:2000, Santa Cruz, Calif., USA); Col6a1(1:1000 Santa Cruz, Calif., USA); and Spp1 (1:200 Santa Cruz, Calif., USA).

Human COL6A1 was cloned into pBABE hygromycin vectors and transgenic cells made as described herein.

Transcript levels in Runx3-overexpressing carcinoma cells were determined using qRT-PCR as described herein. The Spp1 mouse forward and reverse primers used were SEQ ID NO.:5 (TTTCACTCCAATCGTCCCTACA) and SEQ ID NO.:6 (TCAGTCCATAAGCCAAGCTATCA), respectively; the Col6A1 mouse forward and reverse primers were SEQ ID NO.:7 (CTGCTGCTACAAGCCTGCT) and SEQ ID NO.:8 (CTGCTGCTACAAGCCTGCT), respectively; and the COL6A1 human forward and reverse primers were SEQ ID NO.:9 (ACACCGACTGCGCTAT-CAAG) and SEQ ID NO.:10 (CGGTCACCACAATCAG-GTACTT), respectively.

For luciferase assays, the human COL6A1 promoter region was subcloned into a pGL2 vector from a Bac clone (ID RP11-892E8) obtained from Children's Hospital Oakland Research Institute, USA. For SPP1 and COL6A1 assays, 0.1-0.3 µg of promoter DNA, together with human Flag-RUNX3 or Flag vector, were transfected into HEK293T cells. Cell lysates were prepared at 48 hours in Reporter Lysis Buffer (Promega Wis., USA), substrate added and luciferase activity recorded on a luminometer (Veritas, Wis., USA). β-gal activity was used to normalize the transfection efficiency. Results represent means±SEM of triplicate wells from three independent experiments.

The SPP1 promoter regions were found to have two consensus RUNX3 binding sites and two SMAD binding elements (SBE) in the human (FIG. 11B) and murine genes (data not shown). Similarly, the COL6A1 promoter region was also found to have two RUNX3 consensus-binding sites in the human (FIG. 11D) and murine (data not shown).

Figure 12:
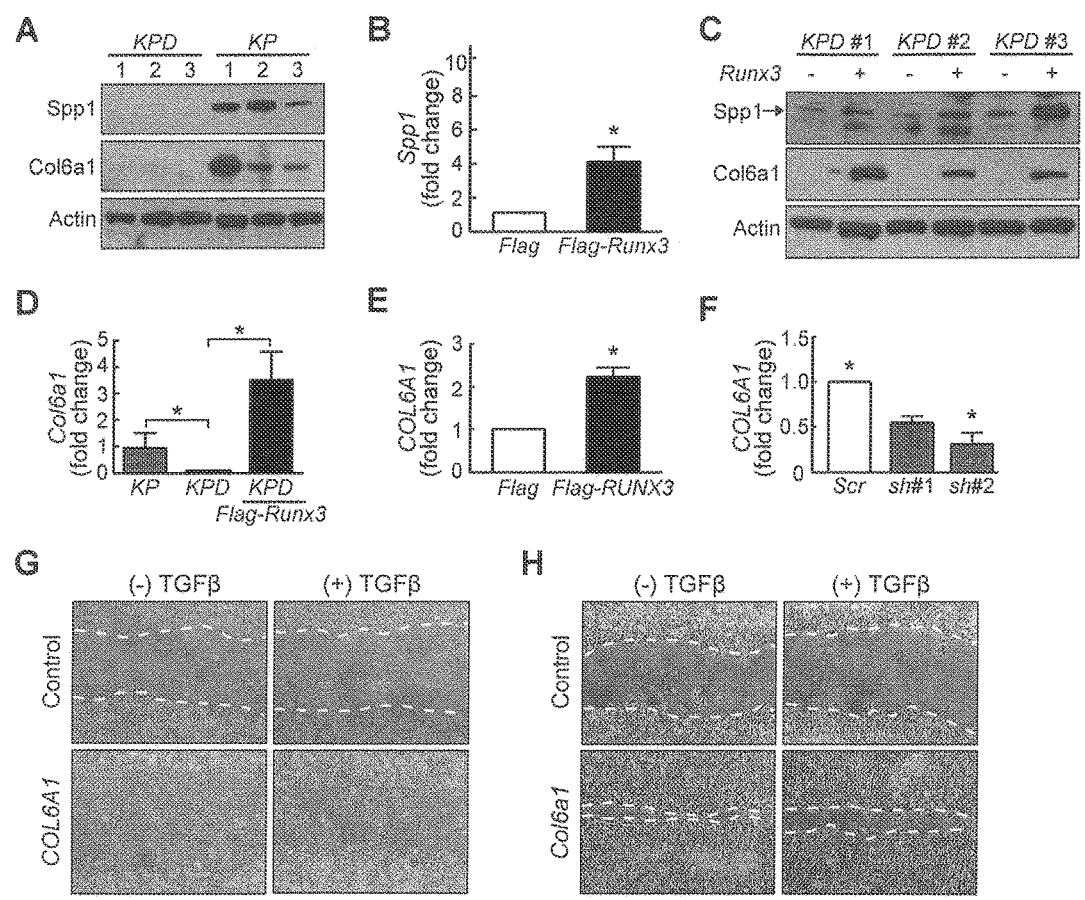

Spp1 was shown to be specifically upregulated in KP as compared to KPD PDA cells (FIG. 12A) and its expression in both murine (FIGS. 12B and 12C) and human PDA cells (FIG. 11C) is sensitive to Runx3. Similarly, Col6a1 was found to be differentially expressed at the protein level in KP and KPD cells (FIG. 12A). Furthermore, luciferase assays confirmed that RUNX3 directly stimulates COL6A1 transcription in both species (FIGS. 12D and 12E). Overexpression of Runx3 correspondingly increases Col6a1 protein levels (shown for murine cells in FIG. 12C), whereas silencing of RUNX3 reduces COL6A1 transcript levels (shown for human cells in FIG. 12F).

Having firmly established the specificity of RUNX3-regulation of COL6A1 levels in both species, COL6A1 was examined for the ability to directly influence behavior in a cell autonomous manner or, in other words, to act as an autocrine enabler of dissemination. Overexpression of COL6A1 in MiaPaca-2 PDA cells (FIG. 12G), and of Col6a1 in KPD carcinoma cells (FIG. 12H), significantly increased their respective migratory abilities in scratch wound migratory assays, and also freed them from a dependence on TGFβ. Thus, in addition to providing a potentially critical component of the three dimensional architecture of a developing tumor, Col6a1 also appears to directly stimulate cell motility.

Overall, these results indicate that RUNX3 serves to both expel the "seed" and prepare the "soil" by directly stimulating cell migration and expressing a host of proteins to remodel the extracellular matrix to favor metastatic colonization.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the

What is claimed is:

1. A method for reducing the risk of pancreatic cancer metastasis, comprising administering to a subject in need thereof an inhibitor of RUNX3 expression or activity.

2. The method of claim 1, wherein the RUNX3 inhibitor comprises a nucleic acid selected from a double-stranded RNA or an antisense RNA.

3. The method of claim 1, further comprising a second method of treatment selected from surgery, chemotherapy, radiation therapy, or any combination thereof.

4. The method according to claim 3 wherein the administration of the RUNX3 inhibitor is performed simultaneously, successively, or concomitantly with the second method of treatment.

5. The method of claim 2, wherein the nucleic acid molecule comprises a sequence as set forth in SEQ ID NO.: 20.

* * * * *